(12) United States Patent
Patrick et al.

(10) Patent No.: US 11,717,411 B2
(45) Date of Patent: Aug. 8, 2023

(54) HYDROGEL IMPLANTS WITH POROUS MATERIALS AND METHODS

(71) Applicant: Cartiva, Inc., Alpharetta, GA (US)

(72) Inventors: Timothy J. Patrick, Roswell, GA (US); Carribeth B. Ramey, Suwanee, GA (US); Letitia Tudor, Suwanee, GA (US); Michael A. Axelrod, Roswell, GA (US)

(73) Assignee: CARTIVA, INC., Alpharetta, GA (US)

( * ) Notice: Subject to any disclaimer, the term of this patent is extended or adjusted under 35 U.S.C. 154(b) by 226 days.

(21) Appl. No.: 17/197,595

(22) Filed: Mar. 10, 2021

(65) Prior Publication Data

US 2021/0220142 A1    Jul. 22, 2021

Related U.S. Application Data

(63) Continuation of application No. 15/909,077, filed on Mar. 1, 2018, now Pat. No. 10,973,644, which is a continuation of application No. 15/085,840, filed on Mar. 30, 2016, now Pat. No. 9,907,663.

(60) Provisional application No. 62/141,059, filed on Mar. 31, 2015.

(51) Int. Cl.
*A61F 2/30* (2006.01)
*A61F 2/38* (2006.01)
(Continued)

(52) U.S. Cl.
CPC ........ *A61F 2/30756* (2013.01); *A61F 2/3872* (2013.01); *A61B 17/86* (2013.01); *A61F 2/3094* (2013.01); *A61F 2/30942* (2013.01); *A61F 2/4618* (2013.01); *A61F 2002/305* (2013.01); *A61F 2002/30011* (2013.01); *A61F 2002/3021* (2013.01); *A61F 2002/30075* (2013.01); *A61F 2002/3085* (2013.01);
(Continued)

(58) Field of Classification Search
CPC ......................... A61F 2/30756; A61F 2/30942
See application file for complete search history.

(56) References Cited

U.S. PATENT DOCUMENTS 3,276,996 A   10/1966 Lazare
3,663,470 A   5/1972 Nishimura et al.
(Continued)

FOREIGN PATENT DOCUMENTS

DE    20218703 U1   3/2003
EP    0222404 A1    5/1987
(Continued)

OTHER PUBLICATIONS

Office Action issued in connection with corresponding Canadian Patent Application No. 2,981,061, dated Mar. 28, 2022, 6 pages.
(Continued)

*Primary Examiner* — Suba Ganesan
(74) *Attorney, Agent, or Firm* — Duane Morris LLP

(57) ABSTRACT

An implant system includes a first portion, a second portion, and a third portion. The first portion includes a hydrogel; the second portion includes a porous material and the hydrogel in pores of the porous material; and the third portion includes the porous material. The first portion is free of the porous material and the third portion is free of the hydrogel. The third portion has non-uniform lateral cross-section.

10 Claims, 14 Drawing Sheets

(51) Int. Cl.
*A61B 17/86* (2006.01)
*A61F 2/46* (2006.01)

(52) U.S. Cl.
CPC ............ *A61F 2002/3092* (2013.01); *A61F 2002/30224* (2013.01); *A61F 2002/30273* (2013.01); *A61F 2002/30299* (2013.01); *A61F 2002/30327* (2013.01); *A61F 2002/30331* (2013.01); *A61F 2002/30462* (2013.01); *A61F 2002/30579* (2013.01); *A61F 2002/30761* (2013.01); *A61F 2002/30841* (2013.01); *A61F 2002/30957* (2013.01); *A61F 2310/00017* (2013.01); *A61F 2310/00023* (2013.01); *A61F 2310/00047* (2013.01); *A61F 2310/00089* (2013.01); *A61F 2310/00185* (2013.01)

(56) References Cited

U.S. PATENT DOCUMENTS

| | | | |
|---|---|---|---|
| 3,673,612 | A | 7/1972 | Merrill et al. |
| 3,849,238 | A | 11/1974 | Gould et al. |
| 3,859,421 | A | 1/1975 | Hucke |
| 4,083,906 | A | 4/1978 | Schindler et al. |
| 4,158,684 | A | 6/1979 | Klawitter et al. |
| 4,205,400 | A | 6/1980 | Shen et al. |
| 4,351,069 | A | 9/1982 | Ballintyn et al. |
| 4,472,542 | A | 9/1984 | Nambu |
| 4,517,295 | A | 5/1985 | Bracke et al. |
| 4,524,064 | A | 6/1985 | Nambu |
| 4,609,337 | A | 9/1986 | Wichterle et al. |
| 4,663,358 | A | 5/1987 | Hyon et al. |
| 4,664,857 | A | 5/1987 | Nambu |
| 4,693,939 | A | 9/1987 | Ofstead |
| 4,731,081 | A | 3/1988 | Tiffany et al. |
| 4,734,097 | A | 3/1988 | Tanabe et al. |
| 4,738,255 | A | 4/1988 | Goble et al. |
| 4,753,761 | A | 6/1988 | Suzuki |
| 4,759,766 | A | 7/1988 | Buttner-Janz et al. |
| 4,772,284 | A | 9/1988 | Suzuki |
| 4,784,990 | A | 11/1988 | Nimrod et al. |
| 4,787,905 | A | 11/1988 | Loi |
| 4,808,353 | A | 2/1989 | Nambu et al. |
| 4,828,493 | A | 5/1989 | Nambu et al. |
| 4,851,168 | A | 7/1989 | Graiver et al. |
| 4,911,720 | A | 3/1990 | Collier |
| 4,916,170 | A | 4/1990 | Nambu |
| 4,946,461 | A | 8/1990 | Fischer |
| 4,988,761 | A | 1/1991 | Ikada et al. |
| 4,995,882 | A | 2/1991 | Destouet et al. |
| 5,047,055 | A | 9/1991 | Bao et al. |
| 5,080,674 | A | 1/1992 | Jacobs et al. |
| 5,095,037 | A | 3/1992 | Iwamitsu et al. |
| 5,106,743 | A | 4/1992 | Franzblau et al. |
| 5,106,876 | A | 4/1992 | Kawamura |
| 5,108,428 | A | 4/1992 | Capecchi et al. |
| 5,108,436 | A | 4/1992 | Chu et al. |
| 5,118,667 | A | 6/1992 | Adams et al. |
| 5,141,973 | A | 8/1992 | Kobayashi et al. |
| 5,171,322 | A | 12/1992 | Kenny |
| 5,171,574 | A | 12/1992 | Kuberasampath et al. |
| 5,192,326 | A | 3/1993 | Bao et al. |
| 5,206,023 | A | 4/1993 | Hunziker |
| 5,219,360 | A | 6/1993 | Georgiade |
| 5,234,456 | A | 8/1993 | Silvestrini |
| 5,244,799 | A | 9/1993 | Anderson |
| 5,258,023 | A | 11/1993 | Reger |
| 5,258,042 | A | 11/1993 | Mehta |
| 5,258,043 | A | 11/1993 | Stone |
| 5,260,066 | A | 11/1993 | Wood et al. |
| 5,287,857 | A | 2/1994 | Mann |
| 5,288,503 | A | 2/1994 | Wood et al. |
| 5,290,494 | A | 3/1994 | Coombes et al. |
| 5,314,477 | A | 5/1994 | Marnay |
| 5,314,478 | A | 5/1994 | Oka et al. |
| 5,326,364 | A | 7/1994 | Clift, Jr. et al. |
| 5,336,551 | A | 8/1994 | Gravier et al. |
| 5,336,767 | A | 8/1994 | Della Valle et al. |
| 5,343,877 | A | 9/1994 | Park |
| 5,344,459 | A | 9/1994 | Swartz |
| 5,346,935 | A | 9/1994 | Suzuki et al. |
| 5,397,572 | A | 3/1995 | Coombes et al. |
| 5,399,591 | A | 3/1995 | Smith et al. |
| 5,401,269 | A | 3/1995 | Buttner-Janz et al. |
| 5,409,904 | A | 4/1995 | Hecht et al. |
| 5,410,016 | A | 4/1995 | Hubbell et al. |
| 5,442,053 | A | 8/1995 | Della Valle et al. |
| 5,458,643 | A | 10/1995 | Oka et al. |
| 5,458,645 | A | 10/1995 | Bertin |
| 5,486,197 | A | 1/1996 | Le et al. |
| 5,489,310 | A | 2/1996 | Mikhail |
| 5,490,962 | A | 2/1996 | Cima et al. |
| 5,492,697 | A | 2/1996 | Boyan et al. |
| 5,494,940 | A | 2/1996 | Unger et al. |
| 5,502,082 | A | 3/1996 | Unger et al. |
| 5,512,475 | A | 4/1996 | Naughton et al. |
| 5,522,898 | A | 6/1996 | Bao |
| 5,534,028 | A | 7/1996 | Bao et al. |
| 5,541,234 | A | 7/1996 | Unger et al. |
| 5,545,229 | A | 8/1996 | Parsons et al. |
| 5,556,429 | A | 9/1996 | Felt |
| 5,556,431 | A | 9/1996 | Buttner-Janz |
| 5,578,217 | A | 11/1996 | Unger et al. |
| 5,601,562 | A | 2/1997 | Wolf et al. |
| 5,626,861 | A | 5/1997 | Laurencin et al. |
| 5,645,592 | A | 7/1997 | Nicolais et al. |
| 5,656,450 | A | 8/1997 | Boyan et al. |
| 5,658,329 | A | 8/1997 | Purkait |
| 5,674,241 | A | 10/1997 | Bley et al. |
| 5,674,295 | A | 10/1997 | Ray et al. |
| 5,674,296 | A | 10/1997 | Bryan et al. |
| 5,688,459 | A | 11/1997 | Mao et al. |
| 5,700,289 | A | 12/1997 | Breitbart et al. |
| 5,705,780 | A | 1/1998 | Bao |
| 5,716,416 | A | 2/1998 | Lin |
| 5,750,585 | A | 5/1998 | Park et al. |
| 5,766,618 | A | 6/1998 | Laurencin et al. |
| 5,769,897 | A | 6/1998 | Harle |
| 5,769,899 | A | 6/1998 | Schwartz et al. |
| 5,789,464 | A | 8/1998 | Muller |
| 5,795,353 | A | 8/1998 | Felt |
| 5,824,093 | A | 10/1998 | Ray et al. |
| 5,824,094 | A | 10/1998 | Serhan et al. |
| 5,844,016 | A | 12/1998 | Sawhney et al. |
| 5,847,046 | A | 12/1998 | Jiang et al. |
| 5,855,610 | A | 1/1999 | Vacant et al. |
| 5,863,297 | A | 1/1999 | Walter et al. |
| 5,863,551 | A | 1/1999 | Woerly |
| 5,876,452 | A | 3/1999 | Anthanasiou et al. |
| 5,876,741 | A | 3/1999 | Ron |
| 5,880,216 | A | 3/1999 | Tanihara et al. |
| 5,882,351 | A | 3/1999 | Fox |
| 5,900,245 | A | 5/1999 | Sawhney et al. |
| 5,916,585 | A | 6/1999 | Cook et al. |
| 5,925,626 | A | 7/1999 | Della Valle et al. |
| 5,928,239 | A | 7/1999 | Mirza |
| 5,935,129 | A | 8/1999 | McDevitt et al. |
| 5,944,754 | A | 8/1999 | Vacanti |
| 5,947,844 | A | 9/1999 | Shimosaka et al. |
| 5,948,829 | A | 9/1999 | Wallajapet et al. |
| 5,957,787 | A | 9/1999 | Hwang |
| 5,976,186 | A | 11/1999 | Bao et al. |
| 5,981,826 | A | 11/1999 | Ku et al. |
| 6,001,352 | A | 12/1999 | Boyan et al. |
| 6,027,744 | A | 2/2000 | Vacanti et al. |
| 6,060,534 | A | 5/2000 | Ronan et al. |
| 6,093,205 | A | 7/2000 | McLeod et al. |
| 6,102,954 | A | 8/2000 | Albrektsson et al. |
| 6,103,255 | A | 8/2000 | Levene et al. |
| 6,132,465 | A | 10/2000 | Ray et al. |
| 6,156,067 | A | 12/2000 | Bryan et al. |
| 6,171,610 | B1 | 1/2001 | Vacanti et al. |
| 6,187,329 | B1 | 2/2001 | Agrawal et al. |
| 6,206,927 | B1 | 3/2001 | Fell |
| 6,224,630 | B1 | 5/2001 | Bao et al. |

(56) References Cited

U.S. PATENT DOCUMENTS

| | | |
|---|---|---|
| 6,231,605 B1 | 5/2001 | Ku |
| 6,245,026 B1 | 6/2001 | Campbell |
| 6,255,359 B1 | 7/2001 | Agrawal et al. |
| 6,264,695 B1 | 7/2001 | Stoy |
| 6,268,405 B1 | 7/2001 | Yao et al. |
| 6,271,278 B1 | 8/2001 | Park et al. |
| 6,280,475 B1 | 8/2001 | Bao et al. |
| 6,337,198 B1 | 1/2002 | Levene et al. |
| 6,340,369 B1 | 1/2002 | Ferree |
| 6,341,952 B2 | 1/2002 | Gayla et al. |
| 6,344,058 B1 | 2/2002 | Ferree |
| 6,355,699 B1 | 3/2002 | Vyakarnam et al. |
| 6,358,251 B1 | 3/2002 | Mirza |
| 6,371,984 B1 | 4/2002 | Van Dyke et al. |
| 6,376,573 B1 | 4/2002 | White et al. |
| 6,379,962 B1 | 4/2002 | Holy et al. |
| 6,383,519 B1 | 5/2002 | Sapieszko et al. |
| 6,402,784 B1 | 6/2002 | Wardlaw |
| 6,402,785 B1 | 6/2002 | Zdeblick et al. |
| 6,419,704 B1 | 7/2002 | Ferree |
| 6,428,576 B1 | 8/2002 | Haldimann |
| 6,451,059 B1 | 9/2002 | Janas et al. |
| 6,472,210 B1 | 10/2002 | Holy et al. |
| 6,482,234 B1 | 11/2002 | Weber et al. |
| 6,531,523 B1 | 3/2003 | Davankov et al. |
| 6,533,818 B1 | 3/2003 | Weber et al. |
| 6,534,084 B1 | 3/2003 | Vyakarnam et al. |
| 6,558,421 B1 | 5/2003 | Fell et al. |
| 6,602,291 B1 | 8/2003 | Ray et al. |
| 6,607,558 B2 | 8/2003 | Kuras |
| 6,610,094 B2 | 8/2003 | Husson |
| 6,629,997 B2 | 10/2003 | Mansmann |
| 6,645,248 B2 | 11/2003 | Casutt |
| 6,667,049 B2 | 12/2003 | Janas et al. |
| 6,679,917 B2 | 1/2004 | Ek |
| 6,686,437 B2 | 2/2004 | Buchman et al. |
| 6,707,558 B2 | 3/2004 | Bennett |
| 6,710,126 B1 | 3/2004 | Hirt et al. |
| 6,726,721 B2 | 4/2004 | Stoy et al. |
| 6,733,533 B1 | 5/2004 | Lozier |
| 6,734,000 B2 | 5/2004 | Chin et al. |
| 6,740,118 B2 | 5/2004 | Eisermann et al. |
| 6,773,713 B2 | 8/2004 | Bonassar et al. |
| 6,783,546 B2 | 8/2004 | Zucherman et al. |
| 6,783,721 B2 | 8/2004 | Higham et al. |
| 6,800,298 B1 | 10/2004 | Burdick et al. |
| 6,802,863 B2 | 10/2004 | Lawson et al. |
| 6,827,743 B2 | 12/2004 | Eisermann et al. |
| 6,840,960 B2 | 1/2005 | Bubb |
| 6,849,092 B2 | 2/2005 | Van Dyke et al. |
| 6,855,743 B1 | 2/2005 | Gvozdic |
| 6,875,232 B2 | 4/2005 | Nigam |
| 6,875,386 B1 | 4/2005 | Ward et al. |
| 6,875,442 B2 | 4/2005 | Holy et al. |
| 6,878,384 B2 | 4/2005 | Cruise et al. |
| 6,881,228 B2 | 4/2005 | Zdeblick et al. |
| 6,893,463 B2 | 5/2005 | Fell |
| 6,893,466 B2 | 5/2005 | Trieu |
| 6,923,811 B1 | 8/2005 | Carl et al. |
| 6,960,617 B2 | 11/2005 | Omidian et al. |
| 6,982,298 B2 | 1/2006 | Calabro et al. |
| 6,993,406 B1 | 1/2006 | Cesarano, III et al. |
| 7,008,635 B1 | 3/2006 | Coury et al. |
| 7,012,034 B2 | 3/2006 | Heide et al. |
| 7,022,522 B2 | 4/2006 | Guan et al. |
| 7,029,479 B2 | 4/2006 | Tallarida et al. |
| 7,048,766 B2 | 5/2006 | Ferree |
| 7,052,515 B2 | 5/2006 | Simonson |
| 7,060,097 B2 | 6/2006 | Fraser et al. |
| 7,066,958 B2 | 6/2006 | Ferree |
| 7,066,960 B1 | 6/2006 | Dickman |
| 7,083,649 B2 | 8/2006 | Zucherman et al. |
| 7,091,191 B2 | 8/2006 | Laredo et al. |
| 7,156,877 B2 | 1/2007 | Lotz et al. |
| 7,186,419 B2 | 3/2007 | Petersen |
| 7,201,774 B2 | 4/2007 | Ferree |
| 7,201,776 B2 | 4/2007 | Ferree et al. |
| 7,214,245 B1 | 5/2007 | Marcolongo et al. |
| 7,217,294 B2 | 5/2007 | Kusanagi et al. |
| 7,235,592 B2 | 6/2007 | Muratoglu et al. |
| 7,250,060 B2 | 7/2007 | Trieu |
| 7,258,692 B2 | 8/2007 | Thelen et al. |
| 7,264,634 B2 | 9/2007 | Schmieding |
| 7,282,165 B2 | 10/2007 | Williams, III et al. |
| 7,291,169 B2 | 11/2007 | Hodorek |
| 7,316,919 B2 | 1/2008 | Childs et al. |
| 7,332,117 B2 | 2/2008 | Higham et al. |
| 7,357,798 B2 | 4/2008 | Sharps et al. |
| 7,377,942 B2 | 5/2008 | Berry |
| 7,682,540 B2 | 3/2010 | Boyan et al. |
| 7,731,988 B2 | 6/2010 | Thomas et al. |
| 7,745,532 B2 | 6/2010 | Ruberti et al. |
| 7,828,853 B2 | 11/2010 | Ek et al. |
| 7,910,124 B2 | 3/2011 | Boyan et al. |
| 7,985,781 B2 | 7/2011 | Muratoglu et al. |
| 8,002,830 B2 | 8/2011 | Boyan et al. |
| 8,142,808 B2 | 3/2012 | Boyan et al. |
| 8,318,192 B2 | 11/2012 | Boyan et al. |
| 8,334,044 B2 | 12/2012 | Myung et al. |
| 8,475,503 B2 | 7/2013 | Denoziere et al. |
| 8,486,436 B2 | 7/2013 | Boyan et al. |
| 8,709,045 B1 | 4/2014 | Folsom |
| 8,895,073 B2 | 11/2014 | Boyan et al. |
| 9,155,543 B2 | 10/2015 | Walsh et al. |
| 9,526,632 B2 | 12/2016 | Walsh et al. |
| 9,545,310 B2 | 1/2017 | Maher et al. |
| 9,737,294 B2 | 8/2017 | Wales et al. |
| 9,907,663 B2 | 3/2018 | Patrick et al. |
| 2001/0016741 A1 | 8/2001 | Burkus et al. |
| 2001/0029399 A1 | 10/2001 | Ku |
| 2001/0038831 A1 | 11/2001 | Park et al. |
| 2001/0039455 A1* | 11/2001 | Simon ............... A61F 2/30767 623/18.11 |
| 2001/0046488 A1 | 11/2001 | Vandenburgh et al. |
| 2002/0026244 A1 | 2/2002 | Trieu |
| 2002/0031500 A1 | 3/2002 | Maclaughlin et al. |
| 2002/0034646 A1 | 3/2002 | Canham |
| 2002/0072116 A1 | 6/2002 | Bhatia et al. |
| 2002/0140137 A1 | 10/2002 | Sapieszko et al. |
| 2002/0173855 A1 | 11/2002 | Mansmann |
| 2002/0183845 A1 | 12/2002 | Mansmann |
| 2002/0183848 A1 | 12/2002 | Ray et al. |
| 2002/0187182 A1 | 12/2002 | Kramer et al. |
| 2003/0008395 A1 | 1/2003 | Holy et al. |
| 2003/0008396 A1 | 1/2003 | Ku |
| 2003/0021823 A1 | 1/2003 | Landers et al. |
| 2003/0055505 A1 | 3/2003 | Sicotte et al. |
| 2003/0059463 A1 | 3/2003 | Lahtinen |
| 2003/0082808 A1 | 5/2003 | Guan et al. |
| 2003/0175656 A1 | 9/2003 | Livne et al. |
| 2003/0176922 A1 | 9/2003 | Lawson et al. |
| 2003/0199984 A1 | 10/2003 | Trieu |
| 2003/0220695 A1 | 11/2003 | Sevrain |
| 2003/0233150 A1 | 12/2003 | Bourne et al. |
| 2003/0236573 A1 | 12/2003 | Evans et al. |
| 2004/0010048 A1 | 1/2004 | Evans et al. |
| 2004/0024465 A1 | 2/2004 | Lambrecht et al. |
| 2004/0034434 A1 | 2/2004 | Evans et al. |
| 2004/0044412 A1 | 3/2004 | Lambrecht et al. |
| 2004/0052867 A1 | 3/2004 | Canham |
| 2004/0059415 A1 | 3/2004 | Schmieding |
| 2004/0059425 A1 | 3/2004 | Schmieding |
| 2004/0063200 A1 | 4/2004 | Chaikof et al. |
| 2004/0064195 A1 | 4/2004 | Herr |
| 2004/0073312 A1 | 4/2004 | Eisermann et al. |
| 2004/0092653 A1 | 5/2004 | Ruberti et al. |
| 2004/0117022 A1 | 6/2004 | Marnay et al. |
| 2004/0143327 A1 | 7/2004 | Ku |
| 2004/0143329 A1 | 7/2004 | Ku |
| 2004/0143333 A1 | 7/2004 | Bain et al. |
| 2004/0147016 A1 | 7/2004 | Rowley et al. |
| 2004/0171143 A1 | 9/2004 | Chin et al. |
| 2004/0172135 A1 | 9/2004 | Mitchell |
| 2004/0220296 A1 | 11/2004 | Lowman et al. |

(56) References Cited

U.S. PATENT DOCUMENTS

| | | |
|---|---|---|
| 2004/0220669 A1 | 11/2004 | Studer |
| 2004/0220670 A1 | 11/2004 | Eisermann et al. |
| 2004/0249465 A1 | 12/2004 | Ferree |
| 2005/0037052 A1 | 2/2005 | Udipi et al. |
| 2005/0043733 A1 | 2/2005 | Eisermann et al. |
| 2005/0043802 A1 | 2/2005 | Eisermann et al. |
| 2005/0049706 A1 | 3/2005 | Brodke et al. |
| 2005/0055094 A1 | 3/2005 | Kuslich |
| 2005/0055099 A1 | 3/2005 | Ku |
| 2005/0071003 A1 | 3/2005 | Ku |
| 2005/0074877 A1 | 4/2005 | Mao |
| 2005/0079200 A1 | 4/2005 | Rathenow et al. |
| 2005/0090901 A1 | 4/2005 | Studer |
| 2005/0096744 A1 | 5/2005 | Trieu et al. |
| 2005/0106255 A1 | 5/2005 | Ku |
| 2005/0137677 A1 | 6/2005 | Rush |
| 2005/0137707 A1 | 6/2005 | Malek |
| 2005/0143826 A1 | 6/2005 | Zucherman et al. |
| 2005/0149196 A1 | 7/2005 | Zucherman et al. |
| 2005/0154462 A1 | 7/2005 | Zucherman et al. |
| 2005/0154463 A1 | 7/2005 | Trieu |
| 2005/0169963 A1 | 8/2005 | Van Dyke et al. |
| 2005/0171608 A1 | 8/2005 | Peterman et al. |
| 2005/0177238 A1 | 8/2005 | Khandkar et al. |
| 2005/0209704 A1 | 9/2005 | Maspero et al. |
| 2005/0216087 A1 | 9/2005 | Zucherman et al. |
| 2005/0228500 A1 | 10/2005 | Kim et al. |
| 2005/0233454 A1 | 10/2005 | Nies et al. |
| 2005/0244449 A1 | 11/2005 | Sayer et al. |
| 2005/0260178 A1 | 11/2005 | Vandenburgh et al. |
| 2005/0261682 A1 | 11/2005 | Ferree |
| 2005/0273176 A1 | 12/2005 | Ely et al. |
| 2005/0277921 A1 | 12/2005 | Eisermann et al. |
| 2005/0278025 A1 | 12/2005 | Ku et al. |
| 2005/0287187 A1 | 12/2005 | Mansmann |
| 2006/0002890 A1 | 1/2006 | Hersel et al. |
| 2006/0052874 A1 | 3/2006 | Johnson et al. |
| 2006/0052875 A1 | 3/2006 | Bernero et al. |
| 2006/0052878 A1 | 3/2006 | Schmieding |
| 2006/0058413 A1 | 3/2006 | Leistner et al. |
| 2006/0064172 A1 | 3/2006 | Trieu |
| 2006/0064173 A1 | 3/2006 | Guederian |
| 2006/0083728 A1 | 4/2006 | Kusanagi et al. |
| 2006/0100304 A1 | 5/2006 | Vresilovic et al. |
| 2006/0121609 A1 | 6/2006 | Yannas et al. |
| 2006/0122706 A1 | 6/2006 | Lo |
| 2006/0136064 A1 | 6/2006 | Sherman |
| 2006/0136065 A1 | 6/2006 | Gontarz et al. |
| 2006/0178748 A1 | 8/2006 | Dinger et al. |
| 2006/0200250 A1 | 9/2006 | Ku |
| 2006/0206209 A1 | 9/2006 | Cragg et al. |
| 2006/0224244 A1 | 10/2006 | Thomas et al. |
| 2006/0229721 A1 | 10/2006 | Ku |
| 2006/0235541 A1 | 10/2006 | Hodorek |
| 2006/0241777 A1 | 10/2006 | Partin et al. |
| 2006/0257560 A1 | 11/2006 | Barone et al. |
| 2006/0259144 A1 | 11/2006 | Trieu |
| 2006/0282165 A1 | 12/2006 | Pisharodi |
| 2006/0282166 A1 | 12/2006 | Molz et al. |
| 2006/0287730 A1 | 12/2006 | Segal et al. |
| 2006/0293561 A1 | 12/2006 | Abay |
| 2006/0293751 A1 | 12/2006 | Lotz et al. |
| 2007/0010889 A1 | 1/2007 | Francis |
| 2007/0014867 A1 | 1/2007 | Kusanagi et al. |
| 2007/0032873 A1 | 2/2007 | Pisharodi |
| 2007/0038301 A1 | 2/2007 | Hudgins |
| 2007/0043441 A1 | 2/2007 | Pisharodi |
| 2007/0067036 A1 | 3/2007 | Hudgins et al. |
| 2007/0073402 A1 | 3/2007 | Vresilovic et al. |
| 2007/0093906 A1 | 4/2007 | Hudgins et al. |
| 2007/0106387 A1 | 5/2007 | Marcolongo et al. |
| 2007/0116678 A1 | 5/2007 | Sung et al. |
| 2007/0118218 A1 | 5/2007 | Hooper |
| 2007/0118225 A1 | 5/2007 | Hestad et al. |
| 2007/0134333 A1 | 6/2007 | Thomas et al. |
| 2007/0135922 A1 | 6/2007 | Trieu |
| 2007/0142326 A1 | 6/2007 | Shue |
| 2007/0162135 A1 | 7/2007 | Segal et al. |
| 2007/0164464 A1 | 7/2007 | Ku |
| 2007/0167541 A1 | 7/2007 | Ruberti et al. |
| 2007/0168039 A1 | 7/2007 | Trieu |
| 2007/0173951 A1 | 7/2007 | Wijlaars et al. |
| 2007/0179606 A1 | 8/2007 | Huyghe et al. |
| 2007/0179614 A1 | 8/2007 | Heinz et al. |
| 2007/0179615 A1 | 8/2007 | Heinz et al. |
| 2007/0179617 A1 | 8/2007 | Brown et al. |
| 2007/0179618 A1 | 8/2007 | Trieu et al. |
| 2007/0179620 A1 | 8/2007 | Seaton, Jr. et al. |
| 2007/0179621 A1 | 8/2007 | McClellan, III et al. |
| 2007/0179622 A1 | 8/2007 | Denoziere et al. |
| 2007/0196454 A1 | 8/2007 | Stockman et al. |
| 2007/0202074 A1 | 8/2007 | Shalaby |
| 2007/0203095 A1 | 8/2007 | Sadozai et al. |
| 2007/0203580 A1 | 8/2007 | Yeh |
| 2007/0208426 A1 | 9/2007 | Trieu |
| 2007/0213718 A1 | 9/2007 | Trieu |
| 2007/0213822 A1 | 9/2007 | Trieu |
| 2007/0213823 A1 | 9/2007 | Trieu |
| 2007/0213824 A1 | 9/2007 | Trieu |
| 2007/0213825 A1 | 9/2007 | Thramann |
| 2007/0224238 A1 | 9/2007 | Mansmann et al. |
| 2007/0225823 A1 | 9/2007 | Hawkins et al. |
| 2007/0227547 A1 | 10/2007 | Trieu |
| 2007/0233135 A1 | 10/2007 | Gil et al. |
| 2007/0233259 A1 | 10/2007 | Muhanna et al. |
| 2007/0265626 A1 | 11/2007 | Seme |
| 2007/0270876 A1 | 11/2007 | Kuo et al. |
| 2007/0270970 A1 | 11/2007 | Trieu |
| 2007/0270971 A1 | 11/2007 | Trieu et al. |
| 2007/0276392 A1 | 11/2007 | Beyar et al. |
| 2007/0299540 A1 | 12/2007 | Ku |
| 2008/0004707 A1 | 1/2008 | Cragg et al. |
| 2008/0015697 A1 | 1/2008 | McLeod et al. |
| 2008/0021563 A1 | 1/2008 | Chudzik |
| 2008/0031962 A1 | 2/2008 | Boyan et al. |
| 2008/0045949 A1 | 2/2008 | Hunt et al. |
| 2008/0051889 A1 | 2/2008 | Hodorek |
| 2008/0057128 A1 | 3/2008 | Li et al. |
| 2008/0075657 A1 | 3/2008 | Abrahams et al. |
| 2008/0077242 A1 | 3/2008 | Rea et al. |
| 2008/0077244 A1 | 3/2008 | Robinson |
| 2008/0097606 A1 | 4/2008 | Cragg et al. |
| 2008/0103599 A1 | 5/2008 | Kim et al. |
| 2008/0114367 A1 | 5/2008 | Meyer |
| 2008/0125870 A1 | 5/2008 | Carmichael et al. |
| 2008/0131425 A1 | 6/2008 | Garcia et al. |
| 2008/0145404 A1 | 6/2008 | Hill et al. |
| 2008/0154372 A1 | 6/2008 | Peckham |
| 2008/0166329 A1 | 7/2008 | Sung et al. |
| 2008/0221505 A1 | 9/2008 | Betts |
| 2008/0269908 A1 | 10/2008 | Warburton |
| 2009/0043398 A1 | 2/2009 | Yakimicki et al. |
| 2009/0138015 A1 | 5/2009 | Connor et al. |
| 2009/0177205 A1 | 7/2009 | McCormack et al. |
| 2009/0182421 A1 | 7/2009 | Silvestrini et al. |
| 2010/0161073 A1 | 6/2010 | Thomas et al. |
| 2010/0198258 A1 | 8/2010 | Heaven et al. |
| 2010/0324693 A1 | 12/2010 | Hardenbrook |
| 2010/0324694 A1 | 12/2010 | Hassler et al. |
| 2011/0040332 A1 | 2/2011 | Culbert et al. |
| 2011/0208305 A1 | 8/2011 | Malinin |
| 2011/0270400 A1 | 11/2011 | Kita et al. |
| 2011/0318704 A1 | 12/2011 | Teichmann |
| 2012/0022568 A1 | 1/2012 | Koblish et al. |
| 2012/0053642 A1 | 3/2012 | Lozier et al. |
| 2012/0203346 A1 | 8/2012 | Kraus |
| 2013/0211451 A1 | 8/2013 | Wales et al. |
| 2014/0324169 A1* | 10/2014 | Maher ............... A61L 27/52 |
| | | 264/28 |
| 2015/0351815 A1 | 12/2015 | Wales et al. |
| 2016/0287407 A1 | 10/2016 | Patrick et al. |
| 2016/0302930 A1 | 10/2016 | Axelrod et al. |

(56) References Cited

U.S. PATENT DOCUMENTS

2017/0165074 A1 6/2017 Walsh et al.
2017/0304039 A1 10/2017 Eaves, III et al.

FOREIGN PATENT DOCUMENTS

| | | |
|---|---|---|
| EP | 0222407 A2 | 5/1987 |
| EP | 0346129 A1 | 12/1989 |
| EP | 0505634 A1 | 9/1992 |
| EP | 041001OB1 | 10/1993 |
| EP | 0411105 B1 | 6/1995 |
| EP | 0845480 A1 | 6/1998 |
| EP | 0919209 A1 | 6/1999 |
| EP | 1287796 A1 | 3/2003 |
| EP | 1030697 B1 | 8/2003 |
| EP | 1344538 A1 | 9/2003 |
| EP | 1584338 A2 | 10/2005 |
| EP | 1482996 B1 | 11/2005 |
| GB | 02056882 A | 3/1981 |
| GB | 02128501 A | 5/1984 |
| JP | 02-184580 | 7/1990 |
| JP | 04053843 | 2/1992 |
| JP | 07247365 | 9/1995 |
| JP | 11035732 | 2/1999 |
| JP | 2005-199054 | 7/2005 |
| JP | 2006-101893 | 4/2006 |
| WO | WO90/007545 A2 | 7/1990 |
| WO | WO90/007575 A1 | 7/1990 |
| WO | WO90/010018 A1 | 9/1990 |
| WO | WO93/016664 A1 | 9/1992 |
| WO | WO94/001483 A1 | 1/1994 |
| WO | WO95/025183 A1 | 9/1995 |
| WO | WO97/006101 A1 | 2/1997 |
| WO | WO97/046178 A1 | 12/1997 |
| WO | WO98/002146 A2 | 1/1998 |
| WO | WO98/050017 A1 | 11/1998 |
| WO | WO99/025391 A2 | 5/1999 |
| WO | WO99/034845 A1 | 7/1999 |
| WO | WO00/030998 A1 | 6/2000 |
| WO | WO00/042991 A1 | 7/2000 |
| WO | WO00/062829 A1 | 10/2000 |
| WO | WO00/066191 | 11/2000 |
| WO | WO01/002033 A1 | 1/2001 |
| WO | WO01/022902 A2 | 4/2001 |
| WO | WO01/059160 A1 | 8/2001 |
| WO | WO01/064030 A1 | 9/2001 |
| WO | WO01/070436 A1 | 9/2001 |
| WO | WO01/091822 A1 | 12/2001 |
| WO | WO02/009647 A2 | 2/2002 |
| WO | WO02/030480 A1 | 4/2002 |
| WO | WO02/064182 A3 | 8/2002 |
| WO | WO03/030787 A1 | 4/2003 |
| WO | WO03/092760 A1 | 11/2003 |
| WO | WO04/060554 A1 | 7/2004 |
| WO | WO04/101013 A1 | 11/2004 |
| WO | WO05/077013 A2 | 8/2005 |
| WO | WO05/077304 A1 | 8/2005 |
| WO | WO05/097006 A2 | 10/2005 |
| WO | WO06/018531 A2 | 2/2006 |
| WO | WO06/019634 A1 | 2/2006 |
| WO | WO06/030054 A1 | 3/2006 |
| WO | WO06/034365 A2 | 3/2006 |
| WO | WO 2006/060416 | 6/2006 |
| WO | WO2009052208 | 4/2009 |
| WO | WO 2012/162552 | 11/2012 |

OTHER PUBLICATIONS

Examination Report issued in connection with corresponding European Patent Application No. 20187933.5, dated Feb. 7, 2022, 4 pages.
First Examination Report issued in connection with corresponding Australian Patent Application No. 2021204444, dated Mar. 25, 2022, 3 pages.
Andrade et al. "Water as a Biomaterial" Trans. Am. Soc. Artif. Intern. Organs 19:1 (1973).
Ariga et al. "Immobilization of Microorganisms with PVA Hardened by Iterative Freezing and Thawing" Journal of Fermentation Technology 65(6): pp. 651-658 (1987).
Boyan et al. "Effect of Titanium Surface Characteristics on Chondrocytes and Osteoblasts in Vitro" Cells and Materials vol. 5 No. 4 pp. 323-335 (1995).
Boyan et al. "Osteoblast-Mediated Mineral Deposition in Culture is Dependent on Surface Microtopography" Calcif. Tissue Int. 71:519-529 (2002).
Bray et al. Poly(vinyl alcohol) Hydrogels for Synthetic Articular Cartilage Material M. Biomed. Mater. Res. vol. 7 pp. 431-443.
Brunette "The Effects of Implant Surface Topography on the Behavior of Cells" Int. J. Oral Maxillofac Implants 3:231-240 (1988).
Chen et al. "Boundary layer infusion of heparin prevents thrombosis and reduces neointimal hyperplasia in venous polytetrafluoroethylene grafts without system anticoagulation" J. Vascular Surgery 22:237-247 (1995).
Chu et al. "Polyvinyl Alcohol Cryogel: An Ideal Phantom Material for MR Studies of Arterial Elasticity" Magnetic Resonance in Medicine v. 37 pp. 314-319 (1997).
Hickey et al. "Mesh size and diffusive characteristics of semicrystalline poly(vinyl alcohol) membranes prepared by freezing/thawing techniques" Journal of Membrane Science 107(3) pp. 229-237 (1995).
Hoffman et al. "Interactions of Blood and Blood Components at Hydrogel Interfaces" Ann. New York Acad. Sci. 283:372-382 (1977).
Hunt Knee Simulation Creep and Friction Tests of Poly(Vinyl Alcohol) Hydrogels Manufactured Using Injection Molding and Solution Casting Thesis for M.S. University of Notre Dame (Jul. 2006).
Katta et al. "Friction and wear behavior of poly(vinyl alcohol)/poly(vinyl pyrrolidone) hydrogels for articular cartilage replacement" Journal of Biomedical Materials Research vol. 83A pp. 471-479 (2007).
Kieswetter et al. "The Role of Implant Surface Characteristics in the Healing of Bone" Grit. Rev. Oral Biol. Med. 7(4):329-345 (1996).
Kieswetter et al. "Surface roughness modulates the local production of growth factors and cytokines by osteoblast-like MG-63 cells" Journal of Biomedical Materials Research vol. 32 pp. 55-63.
Kobayashi et al. "Characterization of a polyvinyl alcohol-hydrogel artificial articular cartilage prepared by injection molding" J. Biomater. Sci. Polymer Edn. 15(6): 741-751 (2003).
Kobayashi et al. "Development of an artificial meniscus using polyvinyl alcohol-hydrogel for early return to and continuance of athletic life in sportspersons with severe meniscus injury. I: mechanical evaluation." The Knee 10 (2003); 47-51.
Kohavi et al. "Markers of primary mineralization are correlated with bone-bonding ability of titanium or stainless steel in vivo" Clin. Oral. Impl. Res. 6:1-13 (1995).
Koutsopoulos et al. "Calcification of porcine and human cardiac valves: testing of various inhibitors for antimineralization" J. Mater. Sci. Mater. Med. 9:421-424 (1998).
Kwak BK et al. "Chitin-based Embolic Materials in the Renal Artery of Rabbits: Pathologic Evaluation of an Absorbable Particulate Agent" Radiology 236:151-158 (2005).
Landolt et al. "Electrochemical micromachining polishing and surface structuring of metals: fundamental aspects and new developments" Elsevier Science Ltd. pp. 3185-3201 (2003).
Lazzeri et al. "Physico-chemical and mechanical characterization of hydrogels of poly(vinyl alcohol) and hyaluronic acid" J. Mater. Sci. In Med. 5:862-867 (1994).
Liao et al. "Response of rat osteoblast-like cells to microstructured model surfaces in vitro" Biomaterials 24 pp. 649-654 (2003).
Lozinsky et al. "Study of cryostructurization of polymer systems. VII. Structure formation under freezing of poly(vinyl alcohol) acqueous solutions" Colloid & Polymer Science vol. 264 pp. 19-24 (1986).

(56) References Cited

OTHER PUBLICATIONS

Lozinsky et al. "Study of Cryostructuration of Polymer Systems. XII. Poly(vinyl alcohol) Cryogels: Influence of Low-Molecular Electrolytes" Journal of Applied Polymer Science vol. 61 pp. 1991-1998 (1996).

Lozinsky et al. "Study of Cryostructuration of Polymer Systems. XI. The Formation of PVA Cryogels by Freezing-Thawing the Polymer Aqueous Solutions Containing Additives of Some Polyols" Journal of Applied Polymer Science vol. 58 pp. 171-177 (1995).

Lozinsky et al. "Poly(vinyl alcohol) cryogels employed as matrices for cell immobilization. 2. Entrapped cells resemble porous fillers in their effects on the properties of PVA-cryogel carrier" Enzyme and Microbial Technology vol. 20 No. 3 pp. 182-190 (1997).

Lozinsky et al. "Poly(vinyl alcohol) cryogels employed as matrices for cell immobilization. 3. Overview of recent research and developments" Enzyme and Microbial Technology vol. 23 No. 3-4 pp. 227-242 (1998).

Lusta et al. "Immobilization of fungus *Aspergillus* sp. by a novel cryogel technique for production of extracellular hydrolytic enzymes" Process Biochemistry vol. 35 pp. 1177-1182 (2000).

Ma et al. "Friction Properties of novel PVP/PVA blend hydrogels as artificial cartilage" Journal of Biomedical Materials Research vol. 93A pp. 1016-1019 (2010).

Martin et al. "Effect of titanium surface roughness on proliferation differentiation and protein synthesis of human osteoblast-like cells (MG63)" Journal of Biomedical Materials Research vol. 29 pp. 389-401 (1995).

Nagura et al. "Structure of poly(vinyl alcohol) hydrogel prepared by repeated freezing and melting" Polymer 30:762-765 (1989).

Nakashima et al. "Study on Wear Reduction Mechanisms of Artificial Cartilage by Synergistic Protein Boundary Film Formation" Japan Soc'y of Mech. Eng'r Int'l J. Series C vol. 48 No. 4 pp. 555-561 (2005).

Oka et al. "Development of an Artificial Articular Cartilage" Clinical Materials vol. 6 pp. 361-381 (1990).

Ong et al. "Osteoblast Responses to BMP-2-Treated Titanium In Vitro" The International Journal of Oral & Maxillofacial Implants vol. 12 No. 5 pp. 649-654 (1997).

Peppas et al. "Reinforced uncrosslinked poly(vinyl alcohol) gels produced by cyclic freezing-thawing processes: a short review" Journal of Controlled Release 16(3): 305-310 (1991).

Peppas et al. "Structure of Hydrogels by Freezing-Thawing Cyclic Processing" Bulletin of the American Physical Society 36:582 (1991).

Peppas et al. "Controlled release from poly(vinyl alcohol) gels prepared by freezing-thawing processes" Journal of Controlled Release vol. 18 pp. 95-100 (1992).

Peppas et al. "Ultrapure poly(vinyl alcohol) hydrogels with mucoadhesive drug delivery characteristics" European Journal of Pharmaceutics and Biopharmaceutics 43(1):51-58 (1997).

Ratner et al. Biomaterials Science An Introduction to Materials in Medicine Academic Press pp. 52 53 & 62 (1996).

Ricciardi et al. "Structure and Properties of Poly(vinyl alcohol) Hydrogels Obtained by Freeze/Thaw Techniques" Macromol. Symp. 222: 49-63 (2005).

Schwartz et al. "Underlying Mechanisms at the Bone-Biomaterial Interface" Journal of Cellular Biochemistry 56:340-347 (1994).

Singh et al. "Polymeric Hydrogels: Preparation and Biomedical Applications" J. Sci. Ind. Res. 39:162-171 (1980).

Stauffer et al. "Poly(vinyl alcohol) hydrogels prepared by freezing-thawing cyclic processing" Polymer 33(1818):3932-3936 (1992).

Stewart et al. "Protein release from PVA gels prepared by freezing and thawing techniques" Proc. Int. Symp. Controlled Release Bioact. Mater. 26th 1004-1005 (1999).

Szczesna-Antezak et al. "Bacillus subtilis cells immobilised in PVA-cryogels" Biomolecular Engineering vol. 17 DD. 55-63 (2001).

The American Heritage® Science Dictionary [online] Houghton Mifflin Company 2002 [retrieved on Jun. 3, 2008], Retrieved from the internet: <URL: http://dictionary.reference.com/browse/pore>.

Watase et al. "Rheological and DSC Changes in Poly(vinyl alcohol) Gels Induced by Immersion in Water" Journal of Polymer Science Polym. Phys. Ed 23(9): 1803-1811 (1985).

Watase et al. "Thermal and rheological properties of poly(vinyl alcohol) hydrogels prepared by repeated cycles of freezing and thawing" Makromol. Chem. v. 189 DD. 871-880 (1988).

Willcox et al. "Microstructure of Poly(vinyl alcohol) Hydrogels Produced by Freeze/Thaw Cycling" Journal of Polymer Sciences: Part B: Polymer Physics vol. 37 pp. 3438-3454 (1999).

WordNet® 3.0 [online] Princeton University 2006 [retrieved on Aug. 6, 2008], Retrieved from the Internet: <URL: http://dictionary.reference.com/browse/mesh>.

Yamaura et al. "Properties of Gels Obtained by Freezing/Thawing of Poly(vinyl Alcohol)/Water/Dimethyl Sulfoxide Solutions" J. Appl. Polymer Sci. 37:2709-2718 (1989).

Yokoyama et al. "Morphology and structure of highly elastic poly(vinyl alcohol) hydrogel prepared by repeated freezing-and-melting" Colloid & Polymer Science vol. 264 No. 7 pp. 595-601 (1986).

Zheng-Qiu et al. "The development of artificial articular cartilage—PVA-hydrogel" Bio-Medical Materials and Engineering vol. 8 pp. 75-81 (1998).

Search Report issued in connection with corresponding European Patent Application No. 20187933.5, dated Nov. 12, 2020, 8 pages.

* cited by examiner

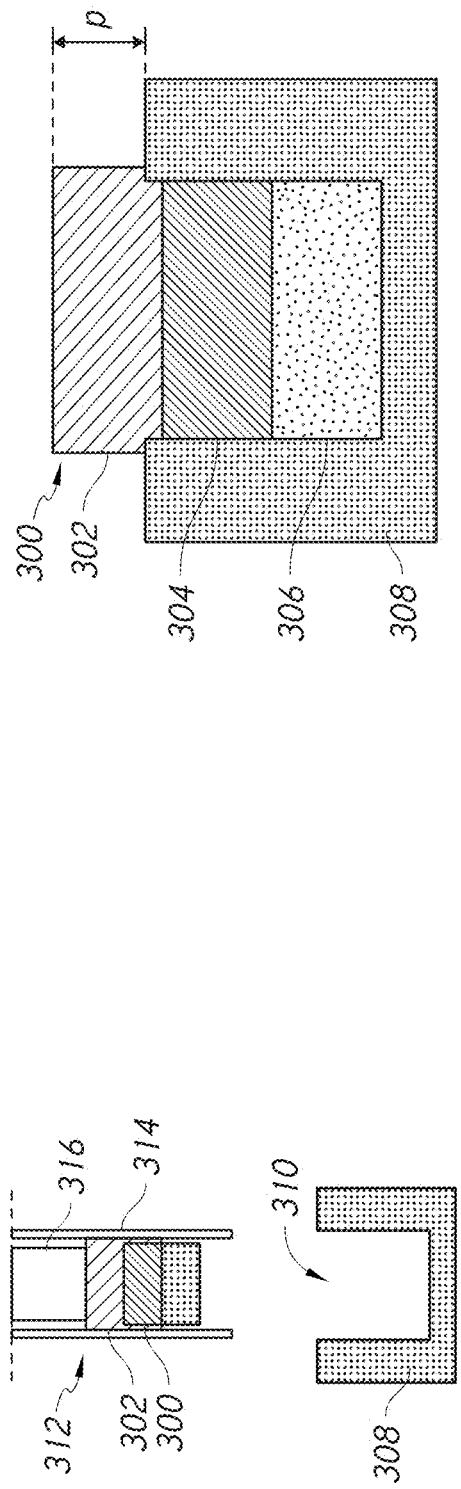
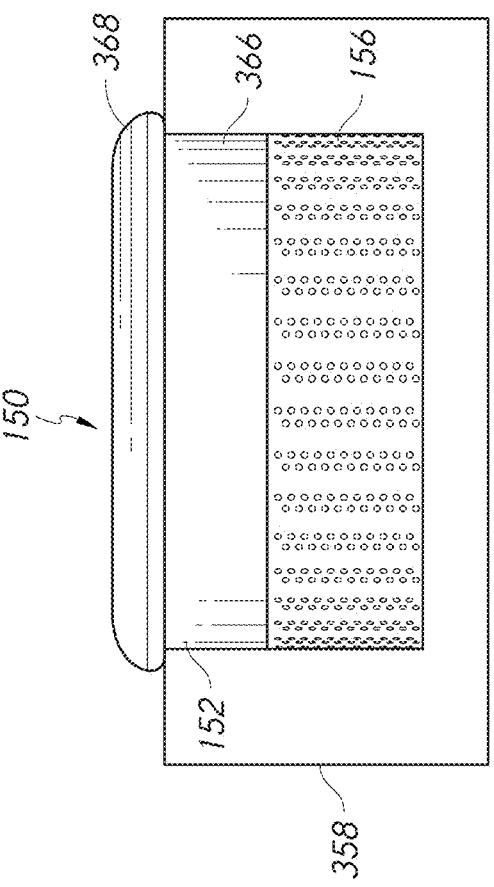
FIG. 3B
FIG. 3C
FIG. 3A

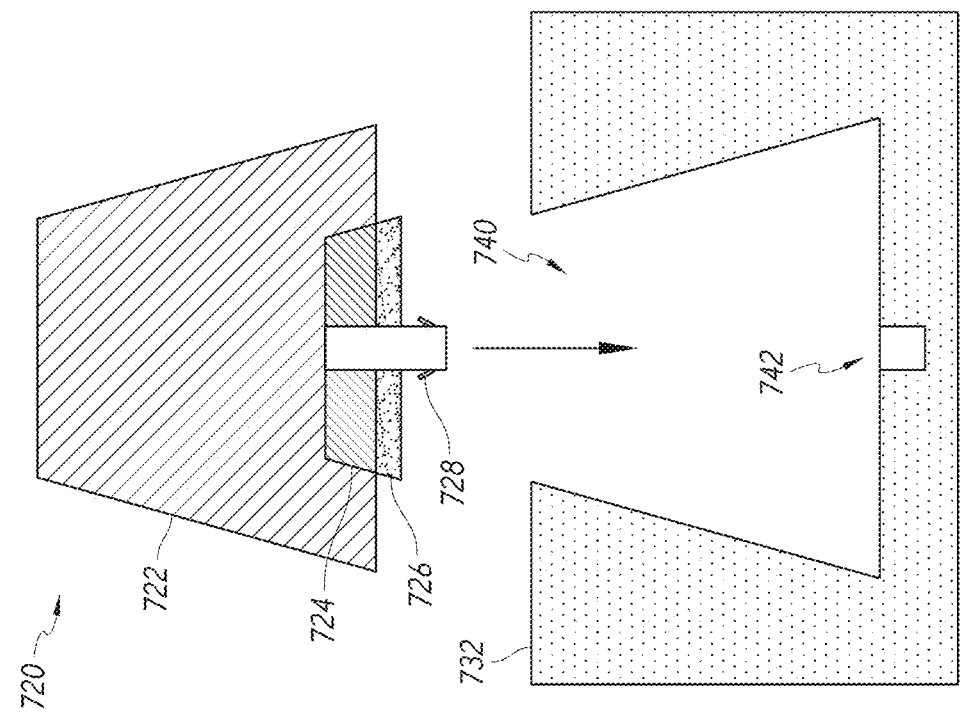
FIG. 7C
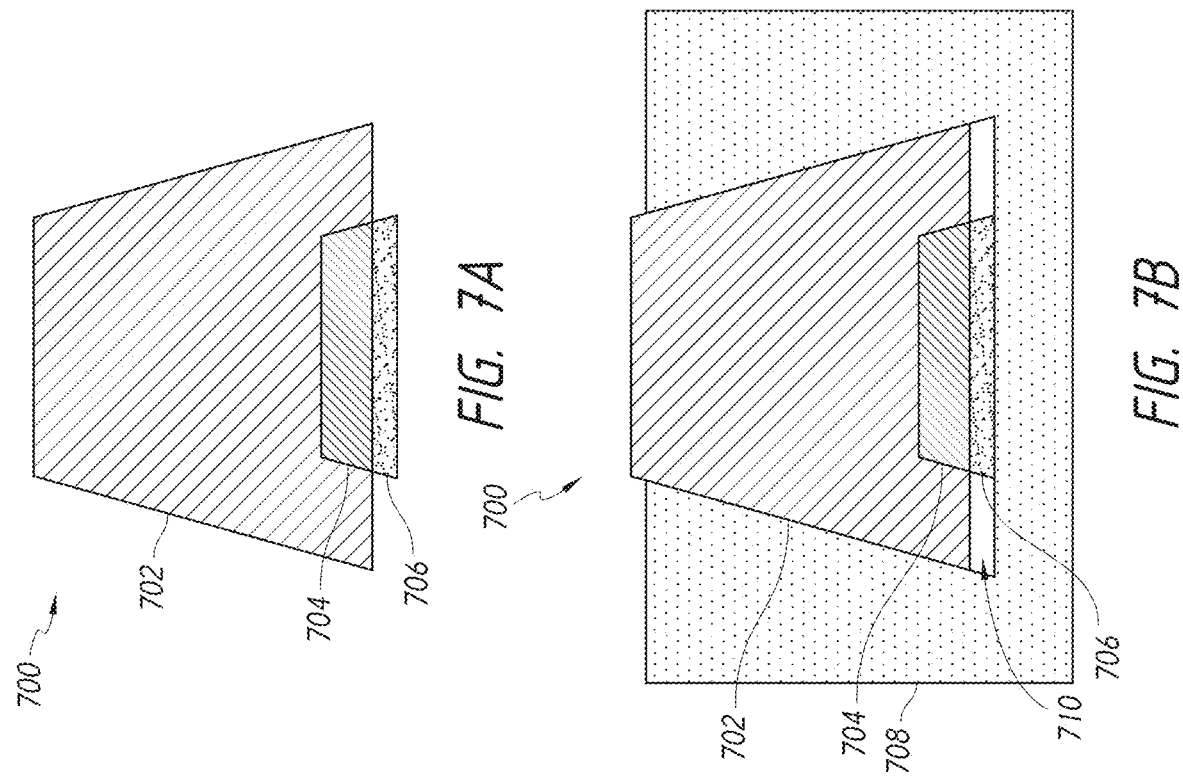
FIG. 7A
FIG. 7B

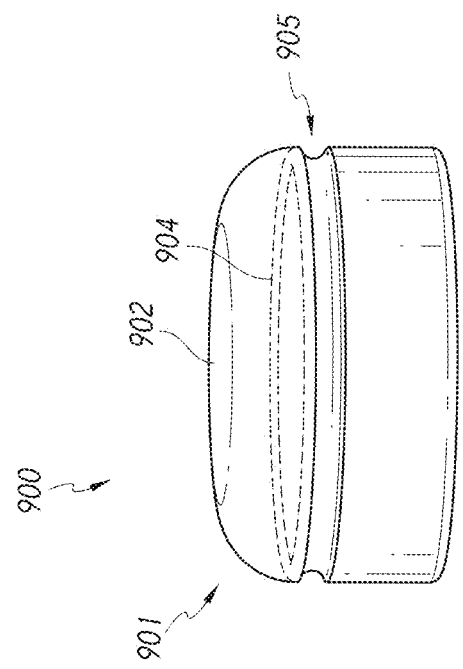
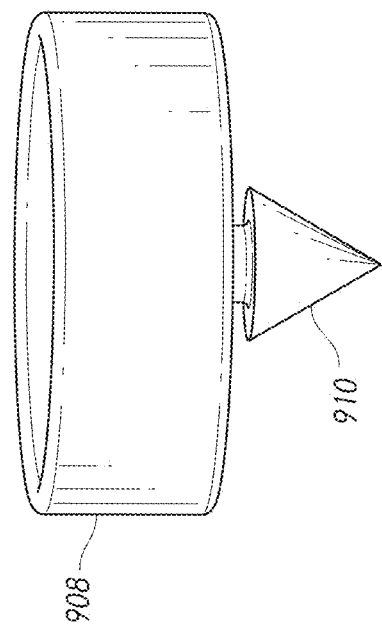
FIG. 9C
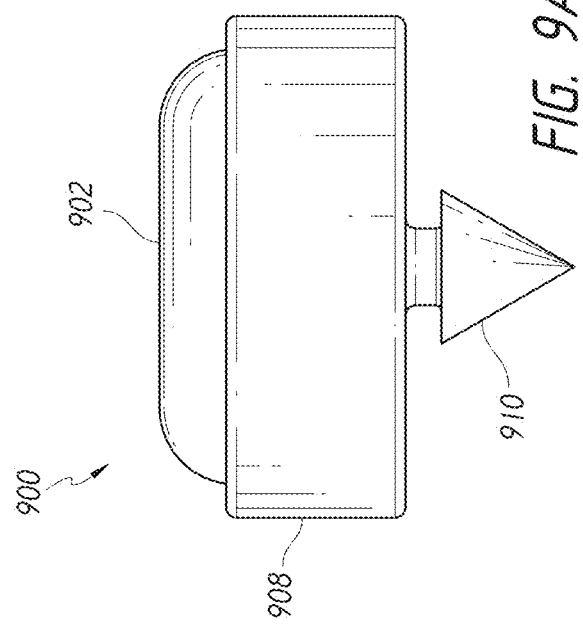
FIG. 9A
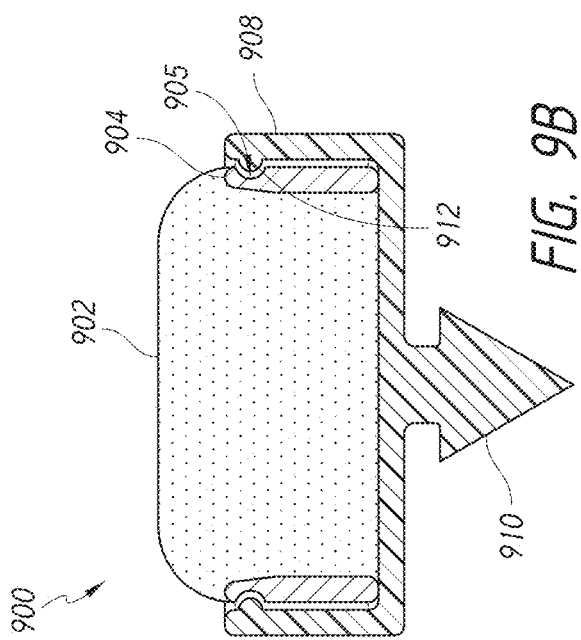
FIG. 9B

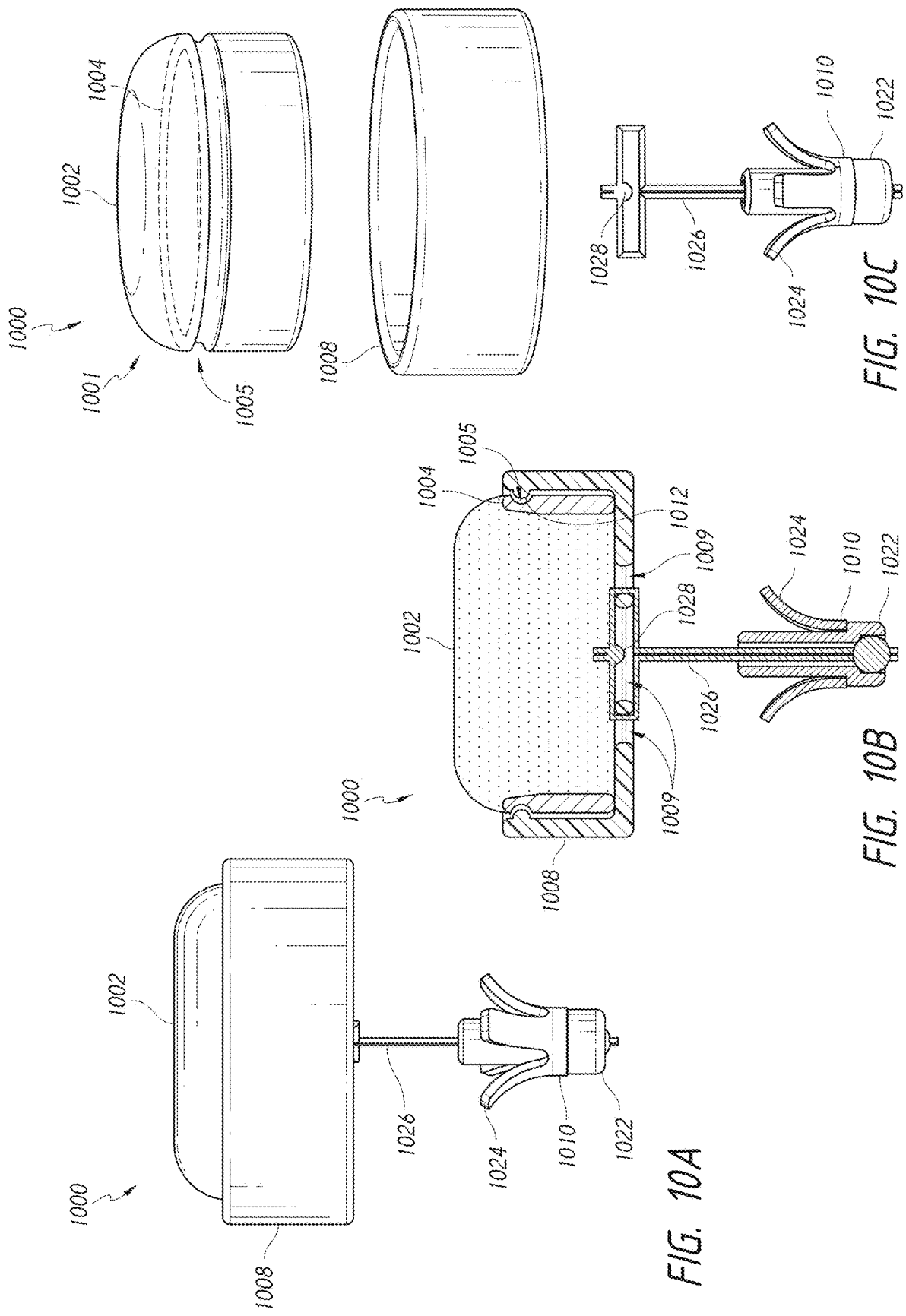

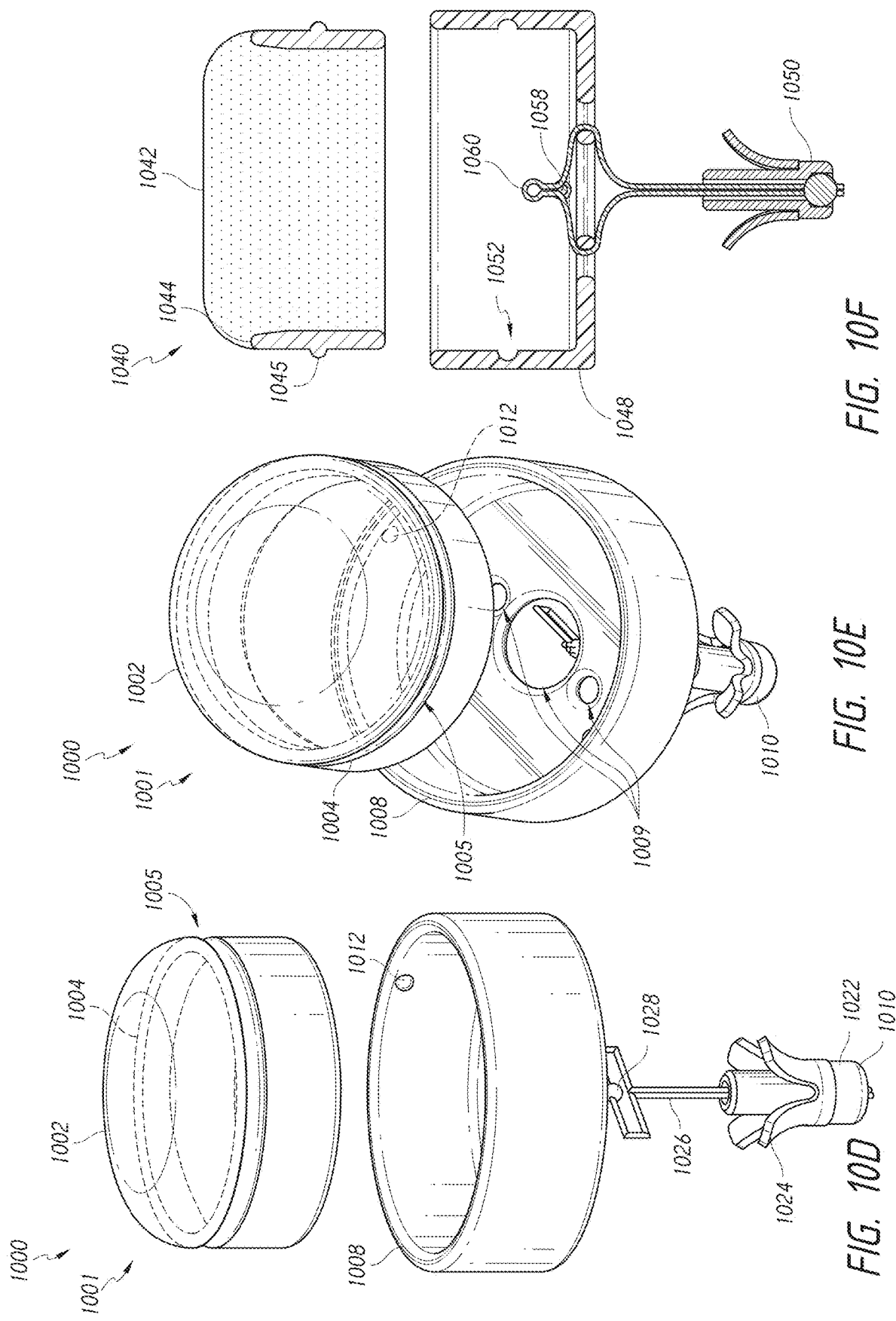

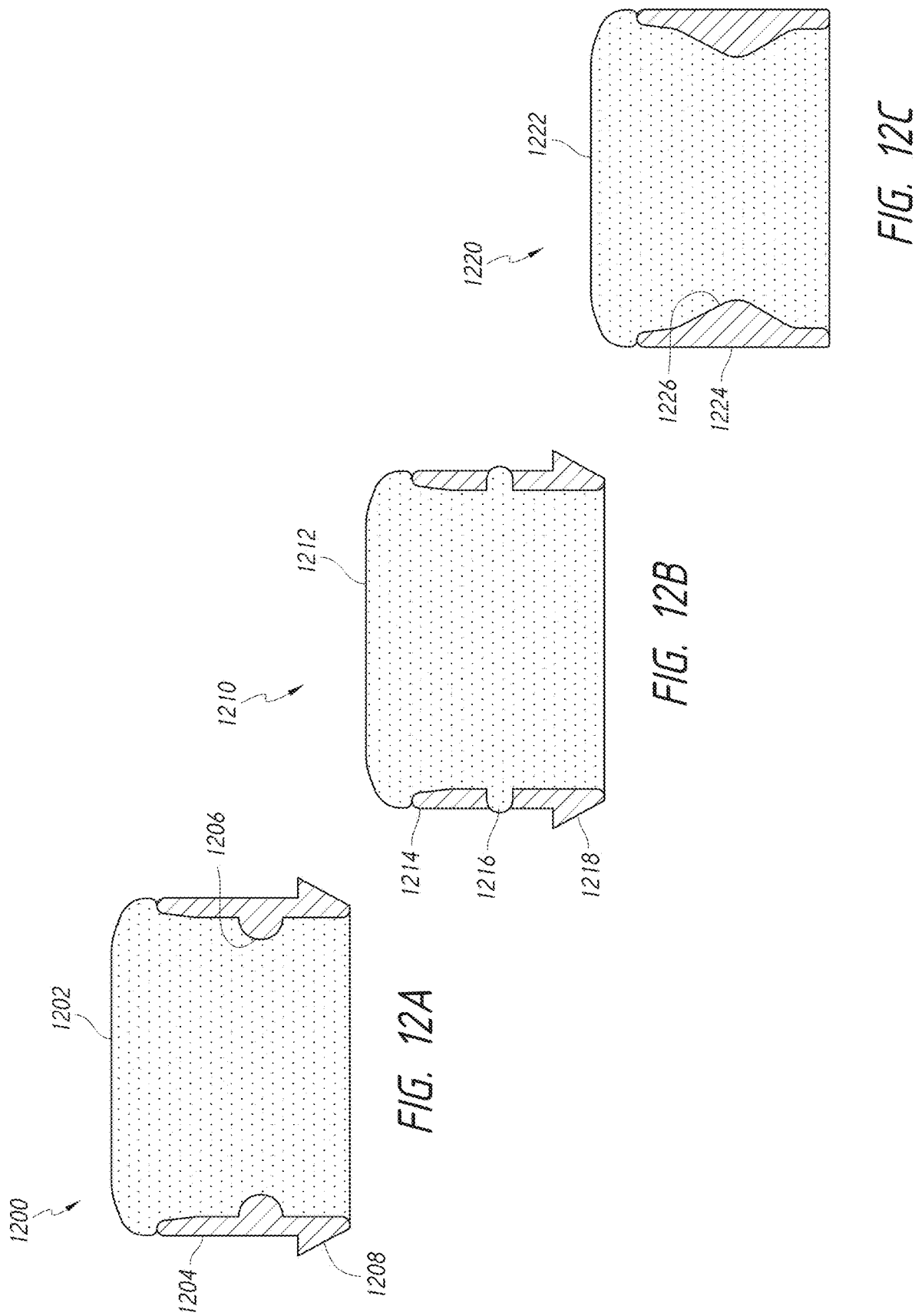

HYDROGEL IMPLANTS WITH POROUS MATERIALS AND METHODS

CROSS-REFERENCE TO RELATED APPLICATIONS

The present application is a continuation of U.S. patent application Ser. No. 15/909,077, filed Mar. 1, 2018 which is a continuation of U.S. patent application Ser. No. 15/085,840, filed Mar. 30, 2016 and issued as U.S. Pat. No. 9,907,663, which claims priority benefit of U.S. Provisional Patent App. No. 62/141,059, filed on Mar. 31, 2015.

BACKGROUND

Field

This disclosure relates generally to implants, and, more specifically, to hydrogel joint implants and various tools, devices, systems, and methods related thereto.

Description of Related Art

Implants can be used to replace deteriorated or otherwise damaged cartilage within a joint. Such devices can be used to treat osteoarthritis, rheumatoid arthritis, other inflammatory diseases, generalized joint pain, joints damaged in an accident, while damaged participating in athletics, joints damaged due to repetitive use, and/or other joint diseases.

SUMMARY

In some embodiments, an implant configured for implantation in a joint comprises, or alternatively consists essentially of, a first portion, a second portion, and a third portion. The first portion comprises a hydrogel. The second portion comprises a porous material (e.g., ceramic, metal, plastic) and the hydrogel in pores of the porous material. The third portion comprises the porous material. The second portion is between the first portion and the second portion. The first portion is free or substantially free of the porous material. The third portion is free or substantially free of the hydrogel.

The hydrogel may comprise polyvinyl alcohol (PVA). The hydrogel may comprise water. The hydrogel may comprise saline. The porous material may comprise an oxide material. The porous material may comprise at least one of aluminum, alumina, zirconia, titanium, titania, stainless steel, PEEK, and steatite. The porous material may have a porosity between 45 ppi and 80 ppi. Pores of the porous material may have a dimension between 100 µm and 500 µm. The first portion may comprise a contoured surface. The first portion may comprise an annular flange. The third portion may comprise threads. The implant may be load bearing and non-biodegradable. The implant may be configured to be placed in at least one of a toe, finger, ankle, knee, shoulder, hip, or other joint. A lateral dimension of the first portion may be between 6 mm and 10 mm. A lateral dimension of the first portion may be between 5% and 15% larger than a lateral dimension of the third portion. A ratio of a lateral dimension of the first portion to a lateral dimension of the third portion may be between 1.05 and 1.3.

In some embodiments, a method of treatment comprises, or alternatively consists essentially of, aligning an implant deployment tool with a recess in a bone, the recess comprising an opening facing a joint, and deploying the implant out of the implant deployment tool, through the opening, and at least partially in the recess.

After deployment, the implant may be 1 mm to 3 mm proud. The method may further comprise radially compressing the first portion of the implant in the implant deployment tool. The method may further comprise forming the recess. Forming the recess may comprise using a drill bit. Deploying the implant may comprise urging the implant through an interior of the implant deployment tool using a plunger. Deploying the implant may be manual. Deploying the implant may be mechanically assisted. Deploying the implant may comprise screwing the implant into the recess.

In some embodiments, a method of manufacturing the implant comprises, or alternatively consists essentially of, positioning hydrogel material in a well of a mold, positioning porous material in an upper portion of the well and protruding from the well, and freezing and thawing the hydrogel material at least once.

Positioning the porous material may comprise anchoring the porous material.

In some embodiments, a method of manufacturing the implant comprises, or alternatively consists essentially of, aligning a well of a second mold portion with a well of a first mold portion, the well of the first mold portion comprising a porous material, positioning hydrogel material in the well of the second mold portion and partially in the well of the first mold portion, and freezing and thawing the hydrogel material at least once.

The method may further comprise positioning the porous material in the well of the first mold portion. Positioning the hydrogel material may be through a closable port, and further comprising closing the closable port. The method may comprising forming flash between the first mold portion and the second mold portion. The method may further comprise removing the flash. The porous material may comprise a disc shape.

In some embodiments, an implant system configured for implantation in a joint comprises, or alternatively consists essentially of, a first part and a second part. The first part comprises an implant. The implant comprises, or alternatively consists essentially of, a first portion comprising a hydrogel, a second portion comprising a porous material and the hydrogel in pores of the porous material, and a third portion comprising the porous material. The first portion is free of or lacks the porous material. The third portion is free of or lacks the hydrogel. The second part comprises sidewalls, a bottom, a cavity at least partially defined by the sidewalls and the bottom, and an anchoring element. The cavity is configured to at least partially receive the implant. One of the porous material and the sidewalls of the second part comprises a detent and the other of the porous material and the sidewalls of the second part comprises a groove configured to interact with the detent when the implant is at least partially in the cavity of the second part.

The porous material may comprise a toroidal shape. The porous material may comprise a detent extending radially inward. The anchoring element may selected from the group consisting of a barb, and anchor, and a hole in the bottom of the second part and a screw configured to extend through the hole in the bottom of the second part. The anchor may comprise an insert, a finger extending radially outwardly and towards a top of the implant system, a wire threaded through holes in the bottom of the second part, and a knot configured to be tightened upon pulling of ends of the wire.

In some embodiments, an implant system configured for implantation in a joint comprises, or alternatively consists essentially of, a first part and a second part. The first part comprises an implant comprising a first portion comprising a hydrogel, a second portion comprising a porous material and the hydrogel in pores of the porous material, and a third portion comprising the porous material. The first portion is free of or lacks the porous material. The third portion is free of or lacks the hydrogel. The second part comprises sidewalls, a bottom, and a cavity at least partially defined by the sidewalls and the bottom. The cavity is configured to at least partially receive the implant.

One of the porous material and the sidewalls of the second part may comprise a detent and the other of the porous material and the sidewalls of the second part may comprise a groove configured to interact with the detent when the implant is at least partially in the cavity of the second part. The second part may further comprise an anchoring element. The anchoring element may comprise a barb. The anchoring element may comprise an anchor comprising an insert, a finger extending radially outwardly and towards a top of the implant system, a wire threaded through holes in the bottom of the second part, and a knot configured to be tightened upon pulling of ends of the wire. The ends of the wire may form a loop. The anchoring element may comprise a hole in the bottom of the second part and a screw configured to extend through the hole in the bottom of the second part. The anchoring element may comprise a hole in the sidewalls of the second part and a second screw configured to extend through the hole in the sidewalls of the second part.

In some embodiments, an implant system configured for implantation in a joint comprises a first portion comprising a hydrogel, a second portion comprising a porous material and the hydrogel in pores of the porous material, and a third portion comprising the porous material. The first portion is free of or lacks the porous material. The third portion is free of or lacks the hydrogel. The third portion is configured to contact bone. Pores of the porous material are configured to allow bone infiltration.

The first portion may comprise a contoured surface. The contoured surface may be customized for a particular subject based on scan data. The scan data may comprise at least one of computerized tomography, computerized axial tomography, positron emission tomography, and magnetic resonance imaging. The porous material may comprise at least one of aluminum, titanium, and stainless steel. The porous material may comprise titanium mesh. The porous material may comprise printed titanium. The porous material may comprise at least one of alumina, zirconia, titania, and steatite. The porous material may comprise PEEK. The porous material may have a porosity between 45 ppi and 80 ppi. Pores of the porous material may have a dimension between 100 μm and 500 μm. The first portion may comprise a hemispherical shape. The first portion may comprise a wedge shape.

In some embodiments, an implant system configured for implantation in a joint comprises an implant comprising a first portion comprising a hydrogel, a second portion comprising a porous material and the hydrogel in pores of the porous material, and a third portion comprising the porous material. The first portion is free of or lacks the porous material. The third portion is free of or lacks the hydrogel.

The second portion may be between the first portion and the second portion. The hydrogel may comprise polyvinyl alcohol (PVA). The hydrogel may comprise water. The hydrogel may comprise saline. The porous material may comprise an oxide ceramic. The porous material may comprise at least one of aluminum, titanium, and stainless steel. The porous material may comprise titanium mesh. The porous material may comprise printed titanium. The porous material may comprise PEEK. The porous material may comprise at least one of alumina, zirconia, titania, and steatite. The porous material may have a porosity between 45 ppi and 80 ppi. Pores of the porous material may have a dimension between 100 μm and 500 μm. The first portion may comprise an annular flange. The third portion may comprise threads.

The first portion may comprise a contoured surface. The contoured surface may be customized for a particular subject based on scan data. The scan data may comprise at least one of computerized tomography, computerized axial tomography, positron emission tomography, and magnetic resonance imaging.

The first portion may comprise a hemispherical shape. The second portion may comprise a hemispherical shape. The third portion may comprise a cylindrical shape. The first portion may comprise a wedge shape. The third portion may comprise a wedge shape. The porous material may comprise a disc shape. The porous material may comprise a toroidal shape. The porous material may comprise a detent extending radially inward. The porous material may comprise an aperture through a sidewall of the porous material. The hydrogel may at least partially extend through the aperture. The porous material may comprise a finger extending radially outwardly and towards a top of the implant system. The porous material may comprise a barb.

The implant may be load bearing. The implant may be non-biodegradable. The implant system may be configured to be placed in at least one of a toe, finger, ankle, knee, shoulder, hip, or other joint. A lateral dimension of the first portion may be between 6 mm and 10 mm. A lateral dimension of the first portion may be between 5% and 15% larger than a lateral dimension of the third portion. A ratio of a lateral dimension of the first portion to a lateral dimension of the third portion may be between 1.05 and 1.3.

The implant system may further comprise a second part comprising sidewalls, a bottom, and a cavity at least partially defined by the sidewalls and the bottom. The cavity may be configured to at least partially receive the implant. The porous material may comprise a groove extending radially inward and the second part may comprise a detent extending radially inward from the sidewalls of the second part. The detent may be configured to interact with the groove when the implant is at least partially in the cavity of the second part. The porous material may comprise a detent extending radially outward and the second part may comprise a groove extending radially outward into the sidewalls of the second part. The detent may be configured to interact with the groove when the implant is at least partially in the cavity of the second part.

The second part further may comprise an anchoring element. The anchoring element may comprise a barb. The barb may comprise a plurality of barbs. The plurality of barbs may be vertically stacked. The anchoring element may comprise an anchor comprising an insert, a finger extending radially outwardly and towards a top of the implant system, a wire threaded through holes in the bottom of the second part, and a knot configured to be tightened upon pulling of ends of the wire. The ends of the wire may form a loop. The anchoring element may comprise a hole in the bottom of the second part and a screw configured to extend through the hole in the bottom of the second part. The anchoring element may comprises a plurality of holes in the bottom of the second part and a plurality of screws configured to extend through the plurality of holes in the bottom of the second part. The anchoring element may comprise a hole in the sidewalls of the second part and a second screw configured to extend through the hole in the sidewalls of the second part. The anchoring element may comprise a plurality of holes in the sidewalls of the second part and a plurality of second screws configured to extend through the plurality of holes in the sidewalls of the second part.

In some embodiments, a method of treatment comprises, or alternatively consists essentially of, aligning an implant deployment tool with a recess in a bone and deploying the implant out of the implant deployment tool, through the opening, and at least partially in the recess. The recess comprises an opening facing a joint.

After deployment, the implant may be 1 mm to 3 mm proud. The method may further comprise radially compressing the first portion of the implant in the implant deployment tool. The method may further comprise forming the recess. Forming the recess may comprise using a drill bit. Deploying the implant may comprise urging the implant through an interior of the implant deployment tool using a plunger. Deploying the implant may be manual. Deploying the implant may be mechanically assisted. Deploying the implant may comprise screwing the implant into the recess.

In some embodiments, a method of manufacturing the implant comprises positioning hydrogel material in a well of a mold, positioning porous material in an upper portion of the well and protruding from the well, and freezing and thawing the hydrogel material at least once. Positioning the porous material may comprise anchoring the porous material.

In some embodiments, a method of manufacturing the implant comprises aligning a well of a second mold portion with a well of a first mold portion. The well of the first mold portion comprises a porous material. The method further comprises positioning hydrogel material in the well of the second mold portion and partially in the well of the first mold portion and freezing and thawing the hydrogel material at least once. The method may further comprising positioning the porous material in the well of the first mold portion. Positioning the hydrogel material may be through a closable port. The method may further comprise closing the closable port.

The method may comprising forming flash between the first mold portion and the second mold portion. The method may further comprise removing the flash. The porous material may comprises a disc shape. The porous material may comprises a toroidal shape.

BRIEF DESCRIPTION OF THE DRAWINGS

Certain features, aspects, and advantages of the disclosure are described with reference to drawings, which are intended to illustrate, but not to limit, the various inventions disclosed herein. It is to be understood that the attached drawings are for the purpose of illustrating concepts and embodiments of the disclosure and may not be to scale.

FIGS. 3A and 3B schematically illustrate an example method of positioning an example implant;
FIG. 3C schematically illustrates an example method of positioning the example implant of FIG. 1B;
FIG. 7B schematically illustrates an example method of positioning an example implant;
FIG. 7C schematically illustrates an example method of positioning an example implant;
FIG. 9A is a side view of an example implant;
FIG. 9B is a cross-sectional view of the implant of FIG. 9A;
FIGS. 9C and 9D are top and side perspective exploded views of the implant of FIG. 9A;
FIG. 10A is a side view of an example implant;
FIG. 10B is a cross-sectional view of the implant of FIG. 10A;
FIGS. 10C-10E are top and side perspective exploded views of the implant of FIG. 10A;
FIG. 10F is a cross-sectional view of an example implant;
FIG. 12A is a side cross-sectional view of an example implant;
FIG. 12B is a side cross-sectional view of an example implant;
FIG. 12C is a side cross-sectional view of an example implant.

DETAILED DESCRIPTION

The discussion and the figures illustrated and referenced herein describe various embodiments of a cartilage implant, as well as various tools, systems, and methods related thereto. A number of these devices and associated treatment methods are particularly well suited to replace deteriorated or otherwise damaged cartilage within a joint. Such implants are configured to remain within the patient's joint on a long-term basis (e.g., for most or all of the life of the patient or subject), and as such, are configured, in some embodiments, to replace native cartilage. In some embodiments, an implant is configured to be substantially non-biodegradable and/or non-erodable. In some embodiments, an implant is configured to remain within the patient's joint or other portion of the anatomy for a minimum of 10 to 100 years (e.g., about 10 years, about 20 years, about 25 years, about 30 years, about 35 years, about 40 years, about 45 years, about 50 years, about 55 years, about 60 years, about 65 years, about 70 years, about 75 years, about 80 years, about 85 years, about 90 years, about 95 years, about 100 years, duration ranges between the foregoing values, etc.) without losing structural and/or physical properties and/or without losing ability to function as a cartilage replacement component or device. In some embodiments, an implant is configured to remain within the anatomy for greater than 100 years without losing structural and/or physical properties and/or without losing ability to function as a cartilage replacement component. Certain implants described herein can be used to treat osteoarthritis, rheumatoid arthritis, other inflammatory diseases, generalized joint pain, joints damaged in an accident, joints damaged while participating in athletics, joints damaged due to repetitive use, and/or other joint diseases. However, the various devices, systems, methods, and other features of the embodiments disclosed herein may be utilized or applied to other types of apparatuses, systems, procedures, and/or methods, including arrangements that have non-medical benefits or applications.

Certain embodiments described herein may be advantageous because they include one, several, or all of the following benefits: (i) improved osseointegration compared to implants having a hydrogel surface; (ii) improved coupling of disparate implant materials; (iii) improved cavity wall apposition compared to substantially cylindrical implants; (iv) reduced implant height; (v) reduced depth of a bone cavity configured to receive an implant; (vi) improved structural stability; and/or (vii) increased manufacturing flexibility.

Figure 1B:
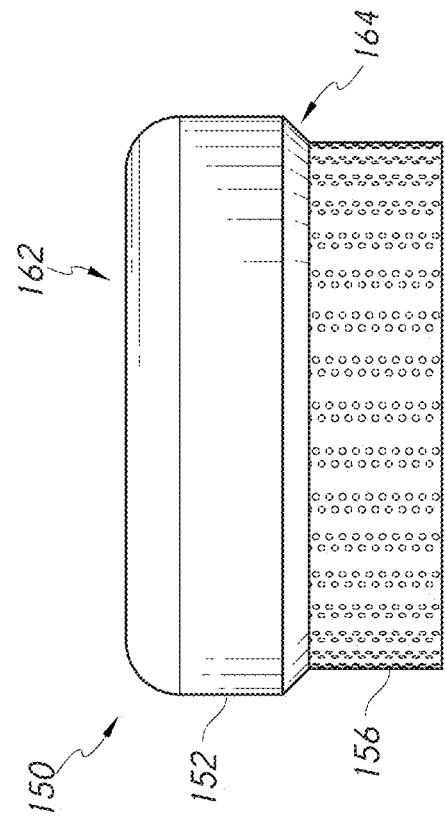
FIG. 1B schematically illustrates an example implant.
Figure 1A:
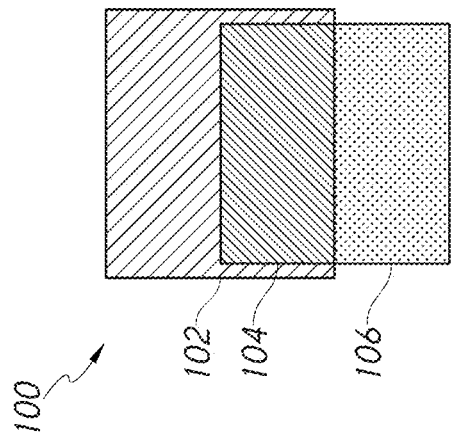
FIG. 1A schematically illustrates an example implant.

FIG. 1A schematically illustrates an example implant 100. The implant 100 comprises, or alternatively consists essentially of, a first portion 102, a second portion 104, and a third portion 106. The first portion 102 and the second portion 104 of the implant 100, as well as other implants disclosed herein (as is the case for each implant feature unless described otherwise), comprises, or alternatively consists essentially of, a hydrogel (e.g., a hydrogel or other formulation comprising polyvinyl alcohol (PVA) hydrogel). The third portion 106 comprises, or alternatively consists essentially of, a porous material (e.g., a material or section comprising porous ceramic material (e.g., oxide-ceramic), metal (e.g., titanium (e.g., titanium mesh, printed titanium), stainless steel (e.g., stainless steel wool)), plastic (e.g., polyaryl ether ketone (PAEK) (e.g., polyether ether ketone (PEEK))), other biocompatible materials, combinations thereof, and the like).

The first portion 102 and the second portion 104 of the implant 100 can comprise one or more other materials, either in addition to or in lieu of PVA, such as, for example, other hydrogels, other polymeric materials, additives, and/or the like. As discussed herein, the second portion 104 comprises porous material. In some embodiments, the PVA content of a hydrogel is about 40% by weight. The PVA content of hydrogel in an implant 100 can be less than or more than about 40% by weight (e.g., about 10%, about 15%, about 20%, about 25%, about 30%, about 32%, about 34%, about 36%, about 37%, about 38%, about 39%, about 41%, about 42%, about 43%, about 44%, about 46%, about 48%, about 50%, about 55%, about 60%, about 65%, about 70%, less than about 10%, more than about 70%, ranges between such values, etc.), as desired or required.

The hydrogel of the implant 100, as well as other implants disclosed herein, can comprise water, saline, other liquids, combinations thereof, and/or the like. In some embodiments, saline may be preferred over water, because, under certain circumstances, saline can help maintain osmotic balance with surrounding anatomical tissues following implantation. The exact composition of hydrogel in an implant 100 (e.g., PVA or other hydrogel materials, water, saline or other liquids, other additives, etc.) can be selected so as to provide the implant 100 with the desired or required strength, load bearing capacity, compressibility, flexibility, longevity, durability, resilience, coefficient of friction, and/or other properties and characteristics. Thus, in some embodiments, any hydrogel portion of the implants disclosed herein consist essentially of saline and PVA. In some embodiments, such hydrogel portions of the implants do not comprise any additional additives (e.g., growth factors, surface or other coatings, etc.). In addition, according to some embodiments, the hydrogel portions of any of the implant configurations disclosed herein comprises a consistent concentration (e.g., no concentration gradients), density and/or other chemical and/or physical properties throughout.

In some embodiments, the implant 100, as well as other implants disclosed herein, is configured for drug delivery and/or is seeded with growth factors and/or cells. In some embodiments, the implant 100 comprises one or more of the following: chondrocytes, growth factors, bone morphogenetic proteins, collagen, hyaluronic acid, nucleic acids, and stem cells. Such factors and/or any other materials included in the implant 100 and selectively delivered to an implant site can help facilitate and/or promote the long-term fixation of the implant 100 at the joint or other target area of the anatomy.

In some embodiments, the hydrogel comprises PVA and/or any other polymeric material. In some embodiments, the content of PVA in the hydrogel is between about 35% and about 45% by weight (e.g., about 35%, about 36%, about 37%, about 38%, about 39%, about 40%, about 41%, about 42%, about 43%, about 44%, about 45%, ranges between such values, etc.). In some embodiments, the content of PVA in the hydrogel is greater than about 45% by weight (e.g., about 45%, about 50%, about 55%, about 60%, about 65%, about 70%, greater than about 70%, ranges between such values, etc.) or less than about 35% by weight (e.g., about 5%, about 10%, about 15%, about 20%, about 25%, about 30%, about 35%, ranges between such values, less than about 5%, etc.). In some embodiments, the content of PVA or other component in the hydrogel is about 40% by weight.

In some embodiments, the implant 100 is load bearing and generally non-biodegradable (e.g., non-bioerodable). In some embodiments, the implant 100 is configured for placement in at least one of a toe, finger, ankle, knee, shoulder, hip, or any other joint. In some embodiments, a transition between the upper surface and the sidewalls is generally curved or otherwise smooth.

In some embodiments, the first portion 102 of the implant may have a lateral dimension (e.g., diameter) between about 6 mm and about 10 mm (e.g., about 6 mm, about 7 mm, about 8 mm, about 9 mm, about 10 mm, ranges between such values, etc.), as measured in an uncompressed state. Lateral dimensions smaller than about 6 mm (e.g., between about 2 mm and about 6 mm) and larger than about 10 mm (e.g., between about 10 mm and about 14 mm) are also possible for use in subjects with small or large bones, respectively, and/or for use in joints with small or large bones, respectively.

The third portion 106 of the implant can comprise a porous material, such as, for example, a porous ceramic (e.g., oxide-ceramic), metal (e.g., titanium (e.g., titanium mesh, printed titanium), stainless steel (e.g., stainless steel wool)), plastic (e.g., polyaryl ether ketone (PAEK) (e.g., polyether ether ketone (PEEK))), other biocompatible materials, combinations thereof, and the like). The third portion 106 may be free or substantially free from the hydrogel of the first portion 102. In some embodiments, the third portion 106 is substantially rigid or non-deformable. In some embodiments, the third portion 106 is at least partially deformable. The pores and/or other openings of the third portion 106 may promote osseointegration of the implant 100 in a bone. Compared to an implant consisting essentially of hydrogel, an implant comprising one or more porous materials (e.g., porous ceramic, metal, plastic, etc.) may have a reduced height because the porous ceramic and/or other porous material may provide structural stability and/or because the porous ceramic or other porous material may provide better osseointegration such that less contact with bone provides at least as much osseointegration.

The third portion 106 is illustrated in FIG. 1A as a disc, although other shapes of the third portion 106 are also possible. In some embodiments, the third portion 106 may be toroidal, wedge-shaped, etc., for example as described in further detail herein. In some embodiments, the third portion 106 is substantially rigid, semi-rigid, and/or non-deformable. In some embodiments, the second portion 104 comprises the hydrogel of the first portion 102 within pores of the porous material of the third portion 106. According to some embodiments, the diameter or other lateral dimension of the second portion 104 and/or third portion 106 is smaller than the diameter or other lateral dimension of the first portion 102 of the implant. As discussed herein, this can permit the implant 100 to be radially compressed (e.g., during delivery into a target anatomical site of a subject), especially in embodiments where the first portion 102 is more readily radially compressible than the second portion 104 and/or the third portion 106 (e.g., because of the material(s) included in each portion). For example, in some embodiments, the diameter or other lateral dimension of the second portion 104 and/or third portion 106 is between about 70% and about 95% (e.g., about 70%, about 75%, about 80%, about 85%, about 90%, about 95%, ranges between the foregoing percentages, etc.) of the diameter or other lateral dimension of the first portion 102.

According to some embodiments, the second portion 104 and the third portion 106 may comprise an oxide ceramic, for example oxide ceramics from CeramTec of Laurens, S.C., as provided in Tables 1 and 2, although other materials and combinations of materials are also possible (e.g., non-oxide ceramics, non-ceramics).

TABLE 1

| Property | Units | Alumina (92%) | Alumina (94%) | Alumina (96%) | Alumina (99.5%) I | Alumina (99.5%) II |
|---|---|---|---|---|---|---|
| Density | g/cm$^3$ | 3.65 | 3.6 | 3.7 | 3.9 | 3.9 |
| Hardness | HV 0.5 | 1300 | 1200 | 1350 | 1700 | 1700 |
| Flexural Strength | MPa (k PSI) | 240 (34.8) | 290 (42) | 296 (43) | 310 (45) | 310 (45) |
| Fracture Toughness | MPaxm$^{1/2}$ | 5 | 3 | 4 | 4 | 4 |
| Young's Modulus | GPa (×10$^6$ PSI) | 300 (44) | 289 (42) | 303 (44) | 372 (54) | 376 (54) |
| Shear Modulus | GPa (×10$^6$ PSI) | 120 (17) | 121 (17.5) | 127 (18.5) | 152 (22) | 152 (22) |
| Poisson | | 0.24 | 0.21 | 0.21 | 0.21 | 0.21 |
| Thermal Expansion (300 °C.) | ×10$^{-6}$/°C. | 7.0 | 6.6 | 6.5 | 6.8 | 6.7 |
| Thermal Expansion (700 °C.) | ×10$^{-6}$/°C. | 7.3 | 7.6 | 7.6 | 7.9 | 7.8 |
| Thermal Expansion (1,000 °C.) | ×10$^{-6}$/°C. | 7.5 | 8.2 | 8.1 | 8.3 | 8.2 |
| Thermal Conductivity at 25 °C. | W/mK | 21.0 | 21.0 | 24.0 | 30.0 | 30.0 |
| Volume Resistivity | ohm × cm | >1014 | >1014 | >1014 | >1014 | >1014 |
| Specific Heat | J/gK | 0.96 | 0.8 | 1.1 | 0.8 | 0.8 |
| Dielectric Strength | V/mil | — | 200 | 210 | 230 | 220 |
| Dielectric Constant at 1 MHz | — | — | 9.0 | 9.3 | 9.8 | 9.8 |
| Dissipation Factor at 1 MHz | — | 9.0 × 10$^{-4}$ | 3.0 × 10$^{-4}$ | 3.0 × 10$^{-4}$ | 1.0 × 10$^{-4}$ | 1.0 × 10$^{-4}$ |
| Loss Factor at 1 MHz | — | — | 3.0 × 10$^{-3}$ | 3.0 × 10$^{-3}$ | 1.0 × 10$^{-3}$ | 1.0 × 10$^{-3}$ |

TABLE 2

| Property | Units | Toughened Alumina | Zirconia | Titania | Steatite I | Steatite II |
|---|---|---|---|---|---|---|
| Density | g/cm$^3$ | 4.0 | 6.0 | 4.0 | 2.7 | 2.8 |
| Hardness | HV 0.5 | 1600 | 1150 | 800 | 450 | 420 |
| Flexural Strength | MPa (k PSI) | 448 (65) | 752 (109) | 138 (20) | 131 (19) | 145 (21) |

TABLE 2-continued

| Property | Units | Toughened Alumina | Zirconia | Titania | Steatite I | Steatite II |
|---|---|---|---|---|---|---|
| Fracture Toughness | MPaxm$^{1/2}$ | 4 | 10 | 3 | — | — |
| Young's Modulus | GPa (×10$^6$ PSI) | — | 186 (27) | 227 (33) | 108 (16) | 112 (16) |
| Shear Modulus | GPa (×10$^6$ PSI) | — | 80 (11.6) | 90 (13.0) | 43 (6.3) | 45 (6.5) |
| Poisson | | | 0.33 | 0.27 | 0.23 | 0.25 |
| Thermal Expansion (300 °C.) | ×10$^{-6}$/° C. | 7.9 | — | 8.3 | 8.2 | 6.9 |
| Thermal Expansion (700 °C.) | ×10$^{-6}$/° C. | 8.5 | 10.0 | 9.0 | 8.9 | 7.8 |
| Thermal Expansion (1,000 °C.) | ×10$^{-6}$/° C. | 9.6 | 11.0 | 9.0 | 9.4 | 8.0 |
| Thermal Conductivity at 25 °C. | W/mK | 25.0 | 2.7 | 11.9 | 5.5 | 5.9 |
| Volume Resistivity | ohm × cm | 9.0 × 10$^{13}$ | — | >10$^{12}$ | >10$^{14}$ | >10$^{14}$ |
| Specific Heat | J/gK | 0.96 | 0.4 | 0.7 | 1.1 | 1.1 |
| Dielectric Strength | V/mil | — | — | 100 | 210 | 230 |
| Dielectric Constant at 1 MHz | — | — | 28 | 85 | 5.8 | 6.1 |
| Dissipation Factor at 1 MHz | — | 9.0 × 10$^{-4}$ | — | 5.0 × 10$^{-4}$ | 1.9 × 10$^{-3}$ | 8.0 × 10$^{-4}$ |
| Loss Factor at 1 MHz | — | — | — | — | 1.1 × 10$^{-2}$ | 5.0 × 10$^{-3}$ |

According to some embodiments, the second portion 104 and the third portion 106 may comprise a metal, for example titanium mesh, printed titanium, stainless steel, etc. According to some embodiments, the second portion 104 and the third portion 106 may comprise a plastic, for example PAEK, PEEK, etc.

In some embodiments, the porous material can have a porosity between about 45 pores per inch (ppi) and about 80 ppi (e.g., about 45 ppi, about 50 ppi, about 55 ppi, about 60 ppi, about 65 ppi, about 70 ppi, about 75 ppi, about 80 ppi, ranges between such values, etc.). The pores of the porous material may have a diameter or other dimension between about 100 micrometers (microns; μm) and about 500 μm (e.g., about 100 μm, about 150 μm, about 200 μm, about 250 μm, about 300 μm, about 350 μm, about 400 μm, about 450 μm, about 500 μm, ranges between such values, etc.), as desired or required.

In some embodiments, pores of the porous material in the second portion 104 are different than pores of the porous material in the third portion 106. For example, the pores of the porous material in the second portion 104 may be configured to allow hydrogel infiltration while the pores of the porous material in the third portion 106 may be configured to allow osseointegration. In some embodiments, the porous material in the second portion 104 is different than the porous material in the third portion 106. For example, the porous material in the second portion 104 may comprise a first material having a property and the porous material in the third portion 106 may comprise a second material having a property different than the property of the first material. The property may comprise, for example, the material itself (e.g., whether ceramic, metal, plastic, etc.), porosity, pore size, dimensions, deformability, etc.

Overlap of hydrogel material of the first portion 102 and porous material of the third portion 106 in the second portion 104, for example by the hydrogel material filling pores of the porous material, may securely anchor the first portion 102 to the third portion 106, for example compared to an implant in which a surface of a hydrogel material is adhered to a surface of another material. In some embodiments, a ratio of a height of the second portion 104 to a height of the third portion 106 is between about 1:5 and about 5:1 (e.g., about 1:5, about 1:4, about 1:3, about 1:2, about 1:1, about 2:1, about 3:1, about 4:1, about 5:1, ranges between such values, etc.). In some embodiments, a ratio of a height of the second portion 104 to a height of the ceramic material (e.g., a height of the second portion 104 and a height of the third portion 106) is between about 1:5 and about 1:1.1 (e.g., about 1:5, about 1:4, about 1:3, about 1:2, about 1:1.5, about 1:1.4, about 1:1.3, about 1:1.2, about 1:1.1, ranges between such values, etc.). In some embodiments, a ratio of a height of the third portion 106 to a height of the ceramic material (e.g., a height of the second portion 104 and a height of the third portion 106) is between about 1:5 and about 1:1.1 (e.g., about 1:5, about 1:4, about 1:3, about 1:2, about 1:1.5, about 1:1.4, about 1:1.3, about 1:1.2, about 1:1.1, ranges between such values, etc.).

Compared to an implant consisting essentially of hydrogel, an implant comprising porous material (e.g., porous ceramic, metal, plastic, etc.) may have a reduced height. For example, compared to implants consisting only or essentially of a hydrogel material, such hybrid implants can have a height that is reduced by between about 5% and about 30% (e.g., about 5%, about 10%, about 15%, about 20%, about 25%, about 30%, ranges between the foregoing percentages, etc.). In some embodiments, the third portion 106 of the implant 100 may provide improved or enhanced structural stability to the implant 100. Such improved or enhanced structural stability may be beneficial for use with large bones, although use with small bones is also possible.

Although the implant 100 is schematically illustrated as a cylindrical plug, other shapes of the implant 100 are also possible. For example, an upper surface of the first portion 102 may be contoured to abut particular anatomy (e.g., planar (e.g., flat), non-planar (e.g., curved, concave, convex, undulating, fluted)). The implant 100 can include a generally circular or oval cross-sectional shape. In some embodiments, the implant 100 is generally shaped like a cylinder or a mushroom. The overall shape of any of the implants disclosed herein can vary depending on the specific application or use. For example, the shape of at least part of a portion 102, 104, 106 can be generally polygonal (e.g., rectangular, round, hexagonal), irregular, and/or the like.

Figure 5A:
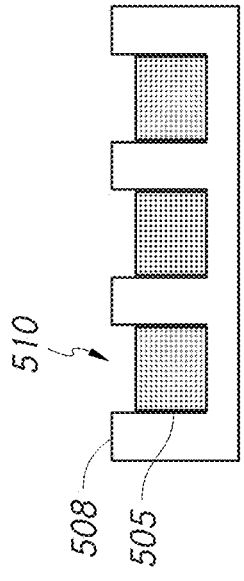
FIGS. 5A-5C schematically illustrate an example method of manufacturing example implants.
Figure 5B:
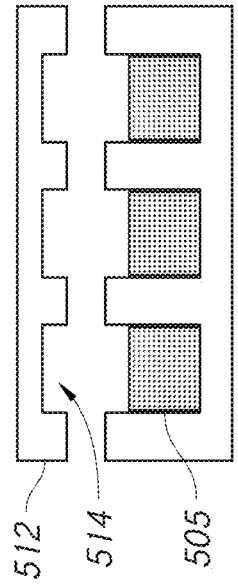
Figure 5C:
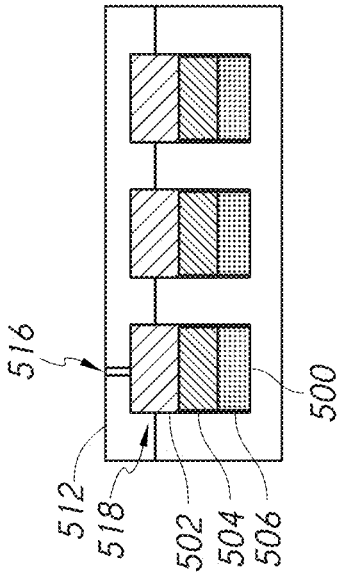
Figure 4:
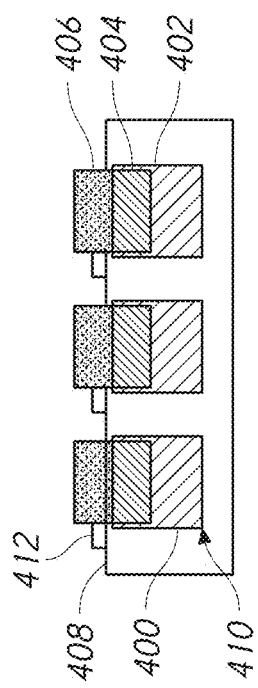
FIG. 4 schematically illustrates an example method of manufacturing example implants.

A molding process, for example as described herein with respect to FIGS. 4 and/or with respect to FIGS. 5A-5C, may be used to form particular shape of an implant 100.

In some embodiments, means for treating a joint (e.g., the implant 100) comprises, or alternatively consists essentially of, means for providing a lubricious surface (e.g., the first portion 102) and means for promoting osseointegration (e.g., the third portion 106).

FIG. 1B schematically illustrates an example implant 150. The implant 150 comprises, or alternatively consists essentially of, a first portion 152, a second portion, and a third portion 156. The first portion 152 and the second portion of the implant 150 comprises, or alternatively consists essentially of, a hydrogel (e.g., a hydrogel or other formulation comprising PVA hydrogel). The second portion is not illustrated due to the opacity of the hydrogel material of the first portion 152. The third portion 156 comprises, or alternatively consists essentially of, a porous material (e.g., a material or section comprising porous ceramic material (e.g., oxide-ceramic), metal (e.g., titanium (e.g., titanium mesh, printed titanium), stainless steel (e.g., stainless steel wool)), plastic (e.g., polyaryl ether ketone (PAEK) (e.g., polyether ether ketone (PEEK))), other biocompatible materials, combinations thereof, and the like). The first portion 152, or the hydrogel material, comprises a contoured upper surface 162. The upper surface 162 may be rounded at the edges and then flat (e.g., as illustrated in FIG. 1B), contoured to correspond to an opposing surface, etc. The hydrogel material of the implant 150 also includes a taper 164 towards the porous material of the third portion 156. Other shapes, surface contours, and combinations thereof are also possible.

Figure 1C:
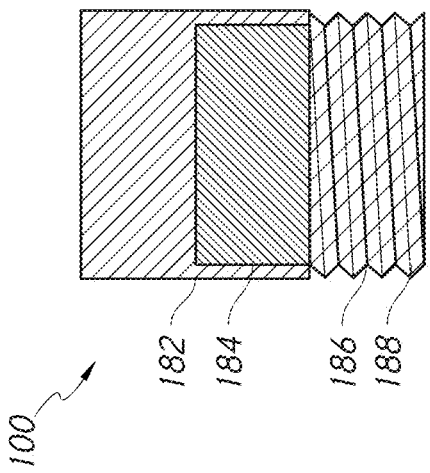
FIG. 1C schematically illustrates an example implant.

FIG. 1C schematically illustrates an example implant 180. The implant 180 comprises, or alternatively consists essentially of, a first portion 182, a second portion 184, and a third portion 186. The third portion 186 comprises threads 188, which can allow the implant to be screwed into bone and/or a hole in bone. The implant 180 may take the shape of a screw. The threads 188 may comprise a same material as the third portion 186 (e.g., porous material) or a different material than the third portion 186 (e.g., a non-porous ceramic, metal, plastic, etc.). Aspects of orthopedic screws, dental implants, etc. such as coatings, surface features, etc. may be integrated into the threads 188 and/or the third portion 186. In some embodiments, the second portion 184 may comprise threads. Threads in the second portion 184 may help, for example, to anchor the hydrogel material to the porous material and/or inhibit relative longitudinal movement therebetween. Threads of the second portion 184 may be the same or different than the threads 188 of the third portion 186.

Figure 2:
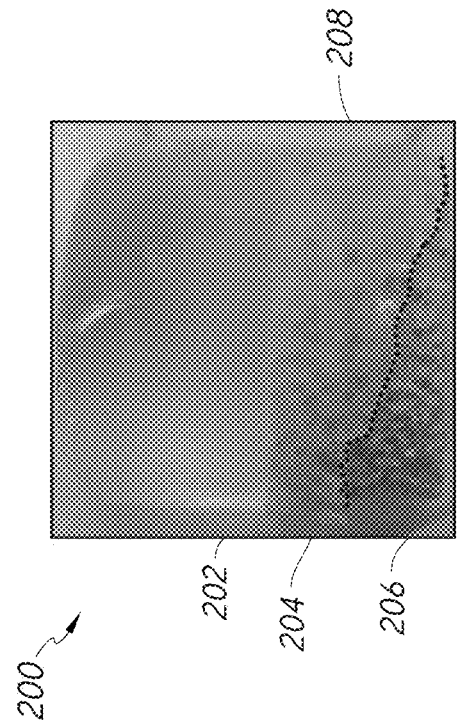
FIG. 2 is a photo of an example implant.

FIG. 2 illustrates one embodiment of an implant 200 comprising a hydrogel section and a porous material section. Similar to the implant 100 discussed above, the illustrated implant 200 comprises a first hydrogel portion 202, a second overlap portion 204, and a third porous material portion 206. In the depicted arrangement, the third portion 206 is substantially free from the hydrogel of the first portion 202, as highlighted by the dotted line 208 between the second portion 204 and the third portion 206. More or less overlap in the second portion 204 is also possible, for example by using less hydrogel material and/or less porous material, by adjusting height of the implant 200, etc. In some embodiments, a ratio of a height of the second portion 204 (e.g., measured at an average of the hydrogel level) to a height of the implant 200 is between about 5% and about 40% (e.g., about 5%, about 10%, about 15%, about 20%, about 25%, about 30%, about 35%, about 40%, ranges between such values, etc.). In some embodiments, a ratio of a height of the second portion 204 to a height of the first portion 202 is between about 15% and about 75% (e.g., about 15%, about 25%, about 35%, about 45%, about 55%, about 65%, about 75%, ranges between such values, etc.). In some embodiments, a ratio of a height of the second portion 204 to a height of the third portion 206 is between about 10% and about 90% (e.g., about 10%, about 20%, about 30%, about 40%, about 50%, about 60%, about 70%, about 80%, about 90%, ranges between such values, etc.).

FIGS. 3A and 3B schematically illustrate an example method of positioning an example implant 300. Similar to the implants 100, 200, the implant 300 comprises a first hydrogel portion 302, a second overlap portion 304, and a third porous material portion 306.

According to some embodiments, the bone portion 308 in which the implant 300 will be positioned has been drilled to form a hole or aperture or recess or cavity or crater or pit or pocket 310. In some embodiments, the lateral dimension (e.g., diameter) of the hole 310 is less than the lateral dimension (e.g., diameter) of the third portion 306, which is rigid. In some embodiments, a lateral dimension and/or cross-sectional area of the hole 310 is about 5% to about 15% (e.g., about 5%, about 6%, about 7%, about 8%, about 9%, about 10%, about 11%, about 12%, about 13%, about 14%, about 15%, ranges between such values, etc.) wider or otherwise larger than the lateral dimension and/or cross-sectional area of the third portion 306. The lateral dimension (e.g., diameter) of the hole 310 may be smaller than the lateral dimension (e.g., diameter) of the first portion 302, which may flex radially inwardly. Although illustrated as a cylindrical hole 310, other shapes are also possible (e.g., trapezoidal tapering inwards towards the upper surface). In some embodiments, a lateral dimension and/or cross-sectional area of the hole 310 is about 5% to about 15% (e.g., about 5%, about 6%, about 7%, about 8%, about 9%, about 10%, about 11%, about 12%, about 13%, about 14%, about 15%, ranges between such values, etc.) narrower or otherwise smaller than the lateral dimension and/or cross-sectional area of the first portion 302. The hole 310 may be coated or otherwise treated prior to positioning of the implant 300.

As a result of the shape of the implant 300 and the corresponding implant site (e.g., in the hole 310), the implant 300 may be inwardly radially compressed in order to insert the implant 300 in the hole 310. A delivery system or introducer 312 and/or other delivery tools can be used to facilitate positioning of the implant 300. Radially inward compressive forces may facilitate delivery of an implant 300 that is at least partially radially oversized relative to the hole

310, as discussed further herein. The degree to which the implant 300 can be compressed (e.g., circumferentially, radially inwardly, etc.) may depend on one or more factors, properties, characteristics and/or other considerations of the first portion 302, such as, for example, implant size, water content, ingredients and other components, strength, elasticity, surrounding temperature, method of manufacturing, and/or the like. Although described herein as generally rigid, the second portion 304 and the third portion 306 may also have some degree of compressibility. Radial compression of an implant 300 can affect the overall height, the shape and/or contours of outer surfaces (e.g., top or articulating surface, base or bottom surface, sides, etc.), and/or one or more other properties or characteristics of the implant 300. In some embodiments, radial compression of an implant 300 causes the height of the implant 300 to increase (e.g., relative to the height of the implant 300 when not radially compressed). Consequently, careful consideration may be given to the design of the implant 300 based on, among other things, the expected level of radial compression that may occur once the implant 300 has been properly secured in the hole 310, prior to implantation. Otherwise, in some embodiments, upon implantation, an implant 300 may not properly align with adjacent cartilage or other tissue surfaces in a joint or other anatomical location.

According to some embodiments, the implant 300 is loaded into a delivery system 312; only the distal end of the delivery system 312 is illustrated in FIG. 3A. The delivery system 312 can comprise an outer body 314 and a plunger or pusher member 316. The outer body 314 may be cylindrical or may taper radially inwardly towards the distal end of the delivery system 312. In the illustrated embodiment, the plunger 316 abuts the first portion 302 of the implant 300. The delivery system 312 can be aligned with the hole 310, and then a user such as a surgeon can depress the plunger 316. The plunger 316 is translatable along the longitudinal axis of the delivery system 312 to push the implant 300 out of the distal end of the delivery system 312 into the hole 310. Depression of the plunger 316 and/or deployment of the implant 300 may be manual, mechanically assisted, combinations thereof, and the like.

FIG. 3B illustrates the implant 300 in the bone portion 308. The hole 310 preferably has a depth that is greater than or equal to the height of the second portion 304 and the third portion 306 such that the part of the implant 300 prolapsing from the bone portion 308, the load-bearing surface, comprises hydrogel and is free or substantially free of the relatively more rigid porous material. In some embodiments, an upper surface of the implant 300 is about 1 millimeter (mm) to about 3 mm above an upper surface of the bone portion 308 (e.g., the bone of the bone portion, remaining cartilage, etc.), also termed "proud," designated in FIG. 3B by the measurement p, which can provide a desired contour of the damaged joint surface. In some embodiments, such a raised or otherwise protruding configuration can assist in creating a smoother transition between the exposed surface of the implant 300 and adjacent native surfaces.

The first portion 302 may have a larger lateral dimension (e.g., diameter) than the third portion 306 to create a "mushroom" shape, as illustrated in FIG. 3B, as well as in FIGS. 1A-2 and other examples herein. In some embodiments, for any of the implants disclosed herein, a ratio of a lateral dimension (e.g., diameter) and/or cross-sectional area of the first portion 302 or a portion thereof to a lateral dimension (e.g., diameter) and/or cross-sectional area of the third portion 306 or a portion thereof is between about 1 and about 1.3 (e.g., greater than or equal to about 1.05, about 1.06, about 1.07, about 1.08, about 1.09, about 1.1, about 1.11, about 1.12, about 1.13, about 1.14, about 1.15, about 1.16, about 1.17, about 1.18, about 1.19, about 1.2, about 1.21, about 1.22, about 1.23, about 1.24, about 1.25, about 1.26, about 1.27, about 1.28, about 1.29, about 1.3, ranges between such values, etc.). In other embodiments, the ratio is between about 1 and 1.05 (e.g., greater than or equal to about 1.01, about 1.02, about 1.03, about 1.04, about 1.05, ranges between such values, etc.), or greater than about 1.3 (e.g., greater than or equal to about 1.3, about 1.35, about 1.4, about 1.45, about 1.5, about 1.55, about 1.6, etc.), as desired or required.

The smaller third portion 306 can slide into the hole 310 of the bone portion 308, although preferably making contact with the sidewalls or perimeter of the hole 310, and the larger first portion 302 can be wedged into the hole 310 of the bone portion 308 due to its flexibility. Referring again to FIG. 3A, the implant 300 may be held in the delivery system 312 by radial compression of the implant 300. The substantially rigid porous material of the second portion 304 and the third portion 306 might not be susceptible to radial compression. The larger first portion 302 can be radially compressed or wedged into the outer body 314 due to its flexibility while the smaller third portion 306 may slide within the outer body 314.

FIG. 3C schematically illustrates an example method of positioning the example implant 150 of FIG. 1B. The implant 150 in a bone portion 358, for example by the method of FIGS. 3A and 3B or another method. The third portion 156 makes contact with the perimeter of the hole in the bone portion 358. The hydrogel material of the second portion and usually the first portion 152 is radially compressed in the hole in the bone portion 358. FIG. 3C illustrates a radially compressed segment 366 and an uncompressed segment 368. The uncompressed segment 368 is over the surface of the bone portion 358. Referring again to FIG. 3B, the segment of the first portion 302 that is proud may be radially larger than the segment of the first portion 302 that is in the hole 310 in the bone portion 308.

FIG. 4 schematically illustrates an example method of manufacturing example implants 400. A mold 408 comprises a plurality of wells or cavities or recesses or holes 410. Bottoms of the wells 410 may be contoured, for example for a specific anatomy location in which an implant 400 will be placed, and/or other factors or considerations. For example, an implant 400 can be configured to generally or specifically match the slopes, contours, and/or other features of the existing cartilaginous and/or bone tissue (e.g., planar (e.g., flat), non-planar (e.g., curved, concave, convex, undulating, fluted)), a recess or hole or cavity created in the bone, and/or the like. Accordingly, the function of a rehabilitated joint or other targeted anatomical region being treated can be improved. The bottom surfaces of the implants 400 in the mold 408 will be the upper load bearing surfaces of the implants 400 in use. In some embodiments, the mold 408 further comprises a plurality of anchors 412 configured to inhibit or prevent third portions 406 from sinking into first portions 402 during the manufacturing process. The anchors 412 may comprise wire, clamps, releasable adhesive, combinations thereof, and the like. Hydrogel material of the first portion 402 fills pores of the porous material of the third portion 406 in the second portion 404. The upper surface of the hydrogel may be generally planar, although other shapes are also possible. A mold configured to make one implant 400 at a time is also possible.

FIGS. 5A-5C schematically illustrate an example method of manufacturing example implants 500. As shown in FIG.

5A, in some embodiments, a first mold portion 508 comprises a plurality of wells or cavities or recesses or holes 510. The first mold portion 508 may be the same or different than the mold 408. In contrast to the method of FIG. 4, the implants 400 are made "upside down" in that the bottom surfaces of the implants 500 in the mold 508 will not be the upper load bearing surfaces of the implants 500 in use. Porous material 505, for example in the shape of discs, grommets, etc., are inserted into the wells 510. Since the porous material 505 are substantially rigid, they will not conform to any contours at bottoms of the wells 510. The fit of the porous ceramic 505 in the mold 508 is preferably tight enough that hydrogel material subsequently inserted into the wells 510 is inhibited or prevented from flowing to bottoms of the wells 510.

As shown in FIG. 5B, a second mold portion 512 comprises a plurality of wells 514 configured to be aligned with the plurality of wells 510 of the first mold portion 508. Bottoms of the wells 514 (or tops of the wells 514 in the orientation of FIG. 5B) may be contoured, for example for a specific anatomical location in which an implant 500 will be placed, and/or other factors or considerations. For example, an implant 500 can be configured to generally or specifically match the slopes, contours, and/or other features of the existing cartilaginous and/or bone tissue (e.g., planar (e.g., flat), non-planar (e.g., curved, concave, convex, undulating, fluted)), a recess or hole or cavity created in the bone, and/or the like. The upper surfaces of the implants 500 will be the upper load bearing surfaces of the implants 500 in use.

As shown in FIG. 5C, the second mold portion 512 is aligned with the first mold portion 508. Hydrogel material can then be inserted into the wells 510, 512, for example through closable port or holes or apertures 516. The hydrogel material fills some but preferably not all of the pores of the porous material 505. Porous material 505 free or substantially free of hydrogel material form the third portions 506, porous material 505 having pores at least partially filled or filled by hydrogel material form the second portions 504, and hydrogel material free or substantially free of porous material 505 form the first portions 502.

The first mold portion 508 and the second mold portion 512 meet at intersection 518. Similar to blow molding processes, any spacing between the mold portions 508, 512 may result in flashing. The molds 508, 512 may be configured to reduce or minimize flashing, for example by being precisely corresponding, tightly joined, etc. The molds 508, 512 may be configured to not reduce flashing, for example by using a flash removal process or by allowing the implants 500 to have flashing.

One or more of the mold portions described with respect to FIGS. 4 and 5A-5C, and modifications thereof, may be tailored to, or designed or customized for, a specific subject's anatomy. For example, a surface of a bone and/or an opposing bone may be scanned (e.g., via computerized tomography (CT), computerized axial tomography (CAT), positron emission tomography (PET), magnetic resonance imaging (MM), combinations thereof, etc.), which can be used to make a mold (e.g., via 3D printing, CAD-CAM milling, etc.) to match specific anatomical features of a specific patient or subject. For example, with reference to FIG. 4, the bottom of the well 410 may be customized such that hydrogel of the first portion 402 takes a certain shape. For another example, with reference to FIGS. 5A-5C, the bottom of the well 514 may be customized such that hydrogel of the first portion 402 takes a certain shape. Other parts of the molds may also be modified (e.g., sides of the wells 410, 514, wells 510, etc.). A custom implant can be advantageous, for example, when the anatomy has been damaged or otherwise includes unique characteristics.

In some embodiments, a scan may reveal that a plurality of implants may be used for treatment. For example, compared to one implant, a plurality of implants may be better able to treat a large defect, be better provide a load bearing surface to key points, and/or provide better access to a physician. The scan can be used to select locations and/or sizes for a plurality of implants. For example, taking a knee joint as an example, a user may select in a scan a portion of a lateral condyle for a first implant and a portion of a medial condyle for a second implant. If the implant would provide an advantage if the portion is a little more anterior, a little more posterior, a little more medial, a little more lateral, etc., the implant can be customized to that particular location using the scan, which may result in, for example, different load bearing surface features, different dimensions, different protrusion amounts, combinations thereof, and the like.

Any of the implant embodiments disclosed herein, or equivalents thereof, can be manufactured using freeze/thaw cycling and/or any other appropriate production method. For example, a hydrogel formulation comprising water, saline, PVA (and/or other hydrogel materials), other polymeric materials, other additives and/or the like can be cooled, heated, and/or otherwise treated as part of a freeze/thaw manufacturing process. In some embodiments, a hydrogel solution comprising saline and about 40% PVA by weight is heated to approximately 121° C. under elevated pressure conditions (e.g., to effect dissolution of the polymer). For example, such a solution can be autoclaved to facilitate complete or substantially complete dissolution of the PVA in the saline, water, and/or other liquid. Next, the temperature and/or pressure of the solution can be lowered to permit entrapped air and/or other gases to escape. In some embodiments, after the autoclaving or similar step, the solution is generally maintained at a temperature of approximately 95° C. and atmospheric pressure for a predetermined time period. The solution can then be transferred (e.g., pumped, poured, etc.) into a mold or mold portions (e.g., as described with respect to FIGS. 4 and 5C) where, once set, form at least part of the shape of the implant.

The molded implant can be removed either after initial formation or after undergoing additional treatment (e.g., freeze/thaw cycling, other heat and/or pressure treatment, etc.). The molded implant may optionally be cut, altered, or otherwise processed after molding. In some embodiments, flashing may be excised and discarded as part of a subsequent reshaping step.

In some embodiments, due in part to the remaining production steps, accommodation of any changes in size (e.g., expansion, contraction, etc.) that may occur or are likely to occur to the implant can be considered during manufacturing by properly sizing and otherwise designing the mold or mold portions. The amount of contraction or expansion of the implant can be based on one or more factors or conditions, such as, for example, the number of freeze/thaw cycles, the temperature and/or pressure ranges associated with the remaining steps, and/or the like.

Other methods can also be used to form the implants described herein. For example, an implant can be formed, at least in part, using an injection molding process and/or any other molding or casting procedure. In such injection or transfer molding techniques, once the hydrogel or other implant solution has been prepared, it can be loaded into an injection cylinder or other container of a molding press. The solution can then be forcibly transferred into a closed mold assembly using a pneumatic or hydraulic ram or any other electromechanical device, system, or method. In some embodiments, the hydrogel and/or other solution or implant component is injected into a corresponding closed mold assembly through a standard runner and gate system. Injection molding of implants can provide one or more benefits relative to open mold assemblies. For instance, an implant formed as part of an injection molding technique may be or may essentially be in a final shape immediately after the injection molding step has been completed such that the manufacturing process may be free or may be substantially free of steps such as post-mold cutting, reshaping, resizing, and/or processing.

Regardless of how the implant is molded or otherwise shaped or manufactured, the implant can be subsequently subjected to one or more freeze/thaw cycles, as desired or required. In some embodiments, the implant, while in a cavity of a mold, is cooled using a total of four freeze/thaw cycles in which the temperature is sequentially varied between about −20° C. and about 20° C. In some embodiments, the number of freeze/thaw cycles, the temperature fluctuation, and/or other details can be different than disclosed herein, in accordance with a specific production protocol and/or implant design.

Following freeze/thaw cycling, the implant can be at least partially removed (e.g., including fully removed) from the mold and placed in one or more saline and/or other fluid (e.g., other liquid) baths where the implant can be subjected to additional cooling and/or other treatment procedures (e.g., to further stabilize the physical properties of the implant). In some embodiments, the implant undergoes an additional eight freeze/thaw cycles while in saline. In some embodiments, such follow-up cooling procedures can be either different (e.g., more or fewer freeze/thaw cycles, different type of bath, etc.) or altogether eliminated from the production process, as desired or required.

When the cooling (e.g., freeze/thaw cycling) and/or other manufacturing processes have been completed, the implants can be inspected for any manufacturing flaws or other defects. At least some of the implants can be subjected to selective testing for physical and other characteristics, in accordance with the original design goals and/or target parameters. The implant may be cut or otherwise processed to remove any excess portions (e.g., flash). In some embodiments, one or more completed implant is packaged in hermetically sealed plastic trays or other containers comprising foil or other types of lids or covering members. A volume of saline and/or other liquid can be included within such trays or other containers to provide hydration of the implant(s) during storage and/or any other steps preceding use. In some embodiments, the implant tray or other container is terminally sterilized using e-beam exposure between about 25 kilogray (kGy) and about 40 kGy.

Additional details related to implants comprising hydrogels, including methods of manufacturing and use, can be found in U.S. Pat. Nos. 5,981,826, 6,231,605, and PCT Patent Application Publication No. WO 2012/162552, each of which is hereby incorporated by reference in its entirety for all purposes.

Figure 6:
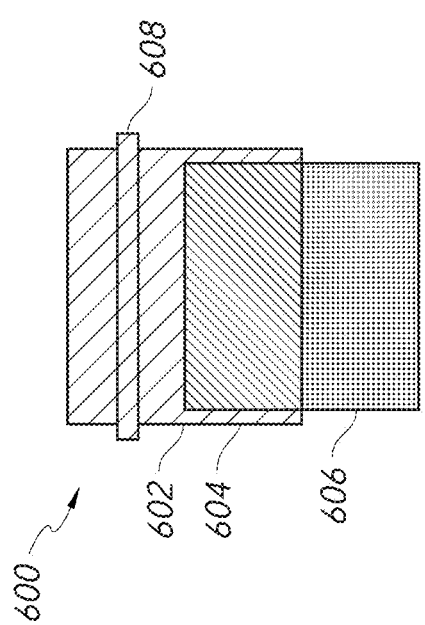
FIG. 6 schematically illustrates another example implant
FIG. 7A schematically illustrates an example implant.

FIG. 6 schematically illustrates another example implant 600. Similar to the implant 100, the implant 600 comprises a first hydrogel portion 602, a second overlap portion 604, and a third porous portion (e.g., comprising porous material) 606. In some embodiments, the implant 600 comprises an outer contour or rim or flange 608. As described with respect to FIG. 5C, the use of a two-part mold may result in flashing where the mold portions 508, 512 meet at intersection 518. The outer contour 608 may comprise unremoved flashing. The outer contour 608 may increase apposition of the first portion 602 in a hole, which can help to anchor the implant 600 in the hole.

FIG. 7A schematically illustrates an example implant 700. Similar to the implant 100, the implant 700 comprises a first hydrogel portion 702, a second overlap portion 704, and a third porous portion (e.g., comprising porous material) 706. The implant 700 comprises outer sidewalls having an angle to the longitudinal axis of the implant 700. In some embodiments, the implant 700 comprises a frustoconical shape. In some embodiments, the implant 700 comprises a pyramid shape. In some embodiments, the porous material in the second portion 704 and the third portion 706 comprises a disc shape, for example as described with respect to the implant 100. In some embodiments, the porous material in the second portion 704 and the third portion 706 comprises a frustoconical or pyramid shape, for example as shown in FIG. 7A. The shape of the porous material and the shape of the hydrogel may be the same (e.g., as illustrated in FIG. 7A) or different (e.g., comprising a disc-shaped porous material).

Implant dimensions, shapes, angles, tooling used to make non-cylindrical bone apertures, tooling to deploy non-cylindrical implants, potential advantages, etc. may be the same as or similar to (e.g., including appropriate modification to include porous material as understood from the present application) the hydrogel implants comprising wedge shapes are described in U.S. Pat. No. 9,155,543, which is hereby incorporated by reference in its entirety for all purposes.

In some embodiments, the porous material may be selected based on bone infiltration characteristics and/or dimensions of the third portion 706. In certain such embodiments, the height and/or shape of the second portion 704 may be at least partially based on a porosity of the porous material. For example, if the porous material is more porous, then hydrogel infiltration into the porous material will be greater, so less porous material may be used. Conversely, if the porous material is less porous, then hydrogel infiltration into the porous material will be less, so more porous material may be used.

FIG. 7B schematically illustrates an example method of positioning an example implant 700. More specifically, FIG. 7B illustrates the implant 700 in a bone portion 708. According to some embodiments, the bone portion 708 in which the implant 700 will be positioned has been drilled to form a hole or aperture or recess or cavity or crater or pit or pocket 710. The hole 710 comprises a shape corresponding to the shape of the implant 700. For example, the hole 710 may be frustoconical, pyramidal, etc. As described in further detail in U.S. Pat. No. 9,155,543, a cylindrical pilot hole may be formed in the bone segment, then a secondary tool may be used to shape the hole 710 such that the hole 710 can take a wide variety of shapes. In some embodiments, the lateral dimension (e.g., diameter) of the top of the hole 710 is greater than the lateral dimension (e.g., diameter) of the bottom of the third portion 706, which is rigid. In some embodiments, a lateral dimension and/or cross-sectional area of the top of the hole 710 is about 5% to about 15% (e.g., about 5%, about 6%, about 7%, about 8%, about 9%, about 10%, about 11%, about 12%, about 13%, about 14%, about 15%, ranges between such values, etc.) wider or otherwise larger than the lateral dimension and/or cross-sectional area of the bottom of the third portion 706. The lateral dimension (e.g., diameter) of the hole 710 may be smaller than the lateral dimension (e.g., diameter) of the bottom of the first portion 702, which may flex radially inwardly. In some embodiments, a lateral dimension and/or cross-sectional area of the top of the hole 710 is about 5% to about 15% (e.g., about 5%, about 6%, about 7%, about 8%, about 9%, about 10%, about 11%, about 12%, about 13%, about 14%, about 15%, ranges between such values, etc.) narrower or otherwise smaller than the lateral dimension and/or cross-sectional area of the bottom of the first portion 702. The hole 710 may be coated or otherwise treated prior to positioning of the implant 700.

The hole 710 preferably has a depth that is greater than or equal to the height of the second portion 704 and the third portion 706 such that the part of the implant 700 prolapsing from the bone portion 708, the load-bearing surface, comprises hydrogel and is free or substantially free of the relatively more rigid porous material. In some embodiments, an upper surface of the implant 700 is about 1 millimeter (mm) to about 7 mm above an upper surface of the bone portion 708 (e.g., the bone of the bone portion, remaining cartilage, etc.), which can provide a desired contour of the damaged joint surface. In some embodiments, such a raised or otherwise protruding configuration can assist in creating a smoother transition between the exposed surface of the implant 700 and adjacent native surfaces.

As a result of the shape of the implant 700 and the corresponding implant site (e.g., in the hole 710), the implant 700 may be inwardly radially compressed in order to insert the implant 700 in the hole 710. A delivery system or introducer and/or other delivery tools can be used to facilitate positioning of the implant 700. Radially inward compressive forces may facilitate delivery of the implant 700 that is at radially oversized relative to the top of the hole 710. The degree to which the implant 700 can be compressed (e.g., circumferentially, radially inwardly, etc.) may depend on one or more factors, properties, characteristics and/or other considerations of the first portion 702, such as, for example, implant size, water content, ingredients and other components, strength, elasticity, surrounding temperature, method of manufacturing, and/or the like. Although described herein as generally rigid, the second portion 704 and the third portion 706 may also have some degree of compressibility. Radial compression of an implant 700 can affect the overall height, the shape and/or contours of outer surfaces (e.g., top or articulating surface, base or bottom surface, sides, etc.), and/or one or more other properties or characteristics of the implant 700. In some embodiments, radial compression of an implant 700 causes the height of the implant 700 to increase (e.g., relative to the height of the implant 700 when not radially compressed). Consequently, careful consideration may be given to the design of the implant 700 based on, among other things, the expected level of radial compression that may occur once the implant 700 has been properly secured in the hole 710, prior to implantation. Otherwise, in some embodiments, upon implantation, an implant 700 may not properly align with adjacent cartilage or other tissue surfaces in a joint or other anatomical location.

Interaction between the sidewalls of the hole 710 and the edges of the implant 700 can create a downward force, which can create a more secure implantation (e.g., resisting dislodge forces). Interaction between the sidewalls of the hole 710 and the edges of the implant 700 can create a downward force, which can help the third portion 706 make contact with the bottom of the hole 710, which can improve bone infiltration into the third portion 706.

In some embodiments, the third portion and the hole may have non-uniform lateral cross-sections. For example, the bottom of the third portion may have an ellipse shape having a length greater than a width, and the top of the hole may have an oval shape having a length greater than a width. During implantation, the implant may be positioned such that the length and width of the third portion are aligned with the length and width of the hole. The generally rigid third portion may fit through the hole when aligned, but the generally rigid third portion may not fit through the hole when the implant is rotated. For example, after rotation, the length of the third portion may not be able to fit through a width of the hole. If the length of an ellipse compared to a circle in a third portion for an otherwise same implant may increase the area of contact between the bottom of the third portion and the bottom of the hole by about 10% to about 50% (e.g., about 10%, about 20%, about 30%, about 40%, about 50%, ranges between such values, etc.). In some embodiments, the implant may be rotated until sides of the third portion make contact with the hole. Contact between sides of the third portion and sides of the hole may provide increased area for bone infiltration and/or increase downward force.

FIG. 7C schematically illustrates an example method of positioning an example implant 720. Similar to the implant 700, the implant 720 comprises a first hydrogel portion 722, a second overlap portion 724, and a third porous portion (e.g., comprising porous material) 726. The implant 700 further comprises an anchor 728. The anchor 728 is illustrated as comprising barbs, but implants comprising other types of anchors compatible with the implant 720 and other implants (e.g., the implants 100, 150, 180, 200, 300, 600, 700, and modifications thereof) are described in further detail herein. For example, the porous material may comprise a grommet shape including an eyelet. The eyelet may be in a center of the porous material or elsewhere, including superficial eyelets in lateral sides of the porous material. The anchor may extend through the eyelet. The porous material may comprise a plurality of eyelets, which may be used for a plurality of anchors and/or for securing a single anchor.

When the implant 720 is inserted into a hole 740 in a bone segment 732 that comprises a secondary hole 742, the anchor 728 can fit into the secondary hole 742. The anchor 728 can flex inwardly during insertion and then is resistant to retraction. The anchor 728 can maintain a downward force on the third portion 726 against the bottom of the hole 740. The force may be advantageous at least until bone infiltration, which may be complete enough to anchor the implant without the anchor 728 in about six to eight weeks. In some embodiments, the secondary hole 742 can be formed while forming a pilot hole (e.g., using a dual diameter drill bit). In some embodiments, the secondary hole 742 can be formed before or after forming a pilot hole (e.g., using a different drill bit), before or after forming a shape such as a wedge. In some embodiments in which a guide pin is used for procedures like drill bit alignment, the secondary hole 742 may be a result of removal of the guide pin.

Figure 8A:
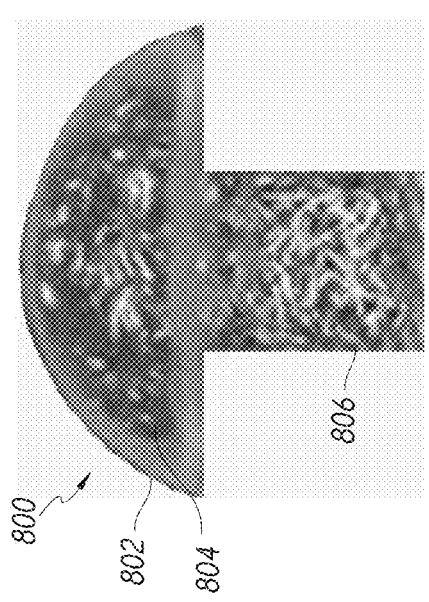
FIG. 8A schematically illustrates an example implant.

FIG. 8A schematically illustrates an example implant 800. Similar to the implant 100, the implant 800 comprises a first hydrogel portion 802, a second overlap portion 804, and a third porous portion (e.g., comprising porous material) 806. As illustrated in FIG. 8A, the porous material comprises a titanium mesh and/or stainless steel wool comprising a bundle of intertwined filaments. The implant 800 comprises a mushroom shape in which the first portion 802 and the second portion 804 are generally hemispherical or dome shaped and the third portion 806 is generally cylindrical. The shape of the porous material in the second portion 802 and the shape of the hydrogel may be the same (e.g., as illustrated in FIG. 8A) or different (e.g., the porous material continuing as a cylinder, being disc shaped in the second portion 804, etc.). In some embodiments, the shape of the first portion 802 corresponds to a load bearing surface, for example a condyle.

Figure 8B:
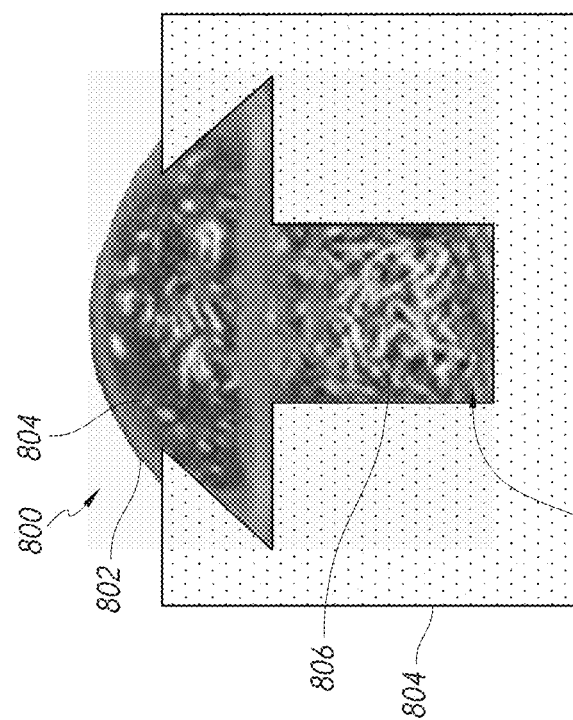
FIG. 8B schematically illustrates an example method of positioning an example implant.

FIG. 8B schematically illustrates an example method of positioning an example implant 800. More specifically, FIG. 8B illustrates the implant 800 in a bone portion 808. According to some embodiments, the bone portion 808 in which the implant 800 will be positioned has been drilled to form a hole or aperture or recess or cavity or crater or pit or pocket 810. The hole 810 comprises a shape corresponding to the shape of the implant 800. For example, the hole 810 may comprise a generally cylindrical lower portion and a wedge shape or spherical segment shape upper portion. As described in further detail in U.S. Pat. No. 9,155,543, a cylindrical pilot hole may be formed in the bone segment, then a secondary tool may be used to shape the hole 810 such that the hole 810 can take a wide variety of shapes. In some embodiments, the lateral dimension (e.g., diameter) of the top of the hole 810 is greater than the lateral dimension (e.g., diameter) of the bottom of the second portion 804, which is relatively rigid. In some embodiments, a lateral dimension and/or cross-sectional area of the top of the hole 810 is about 5% to about 15% (e.g., about 5%, about 6%, about 7%, about 8%, about 9%, about 10%, about 11%, about 12%, about 13%, about 14%, about 15%, ranges between such values, etc.) wider or otherwise larger than the lateral dimension and/or cross-sectional area of the bottom of the second portion 804. The lateral dimension (e.g., diameter) of the hole 810 may be smaller than the lateral dimension (e.g., diameter) of the bottom of the first portion 802, which may flex radially inwardly. In some embodiments, a lateral dimension and/or cross-sectional area of the top of the hole 810 is about 5% to about 15% (e.g., about 5%, about 6%, about 7%, about 8%, about 9%, about 10%, about 11%, about 12%, about 13%, about 14%, about 15%, ranges between such values, etc.) narrower or otherwise smaller than the lateral dimension and/or cross-sectional area of the bottom of the first portion 802. In some embodiments, the lateral dimension (e.g., diameter) of the lower segment of the hole 810 is about the same (e.g., about ±5%, about ±10%, about ±15%, about ±20%, about ±25%) as the lateral dimension (e.g., diameter) of the third portion 806, which is generally rigid but may be flexible or compressible enough to squeeze radially inwardly. In some embodiments, as the third portion 806 is longitudinally compressed, a lateral dimension (e.g., diameter) of the third portion 806 may increase. The hole 810 may be coated or otherwise treated prior to positioning of the implant 800.

The hole 810 preferably has a depth that is greater than or equal to the height of the second portion 804 and the third portion 806 such that the part of the implant 800 prolapsing from the bone portion 808, the load-bearing surface, comprises hydrogel and is free or substantially free of the relatively more rigid porous material. In some embodiments, an upper surface of the implant 800 is about 1 millimeter (mm) to about 7 mm above an upper surface of the bone portion 808 (e.g., the bone of the bone portion, remaining cartilage, etc.), which can provide a desired contour of the damaged joint surface. In some embodiments, such a raised or otherwise protruding configuration can assist in creating a smoother transition between the exposed surface of the implant 800 and adjacent native surfaces.

As a result of the shape of the implant 800 and the corresponding implant site (e.g., in the hole 810), the implant 800 may be inwardly radially compressed in order to insert the implant 800 in the hole 810. A delivery system or introducer and/or other delivery tools can be used to facilitate positioning of the implant 800. Radially inward compressive forces may facilitate delivery of the implant 800 that is at radially oversized relative to the top of the hole 810. The degree to which the implant 800 can be compressed (e.g., circumferentially, radially inwardly, etc.) may depend on one or more factors, properties, characteristics and/or other considerations of the first portion 802, such as, for example, implant size, water content, ingredients and other components, strength, elasticity, surrounding temperature, method of manufacturing, and/or the like. Although described herein as generally rigid, the second portion 804 and the third portion 806 may also have some degree of compressibility. Radial compression of an implant 800 can affect the overall height, the shape and/or contours of outer surfaces (e.g., top or articulating surface, base or bottom surface, sides, etc.), and/or one or more other properties or characteristics of the implant 800. In some embodiments, radial compression of an implant 800 causes the height of the implant 800 to increase (e.g., relative to the height of the implant 800 when not radially compressed). Consequently, careful consideration may be given to the design of the implant 800 based on, among other things, the expected level of radial compression that may occur once the implant 800 has been properly secured in the hole 810, prior to implantation. Otherwise, in some embodiments, upon implantation, an implant 800 may not properly align with adjacent cartilage or other tissue surfaces in a joint or other anatomical location.

Interaction between the sidewalls of the hole 810 and the edges of the implant 810 can create a downward force, which can create a more secure implantation (e.g., resisting dislodge forces). Interaction between the sidewalls of the hole 810 and the edges of the implant 800 can create a downward force, which can help the third portion 806 make contact with the bottom of the hole 810, which can improve bone infiltration into the third portion 806. The sides of the third portion 806 may appose the sidewalls of the lower segment of the hole 810 and contact the bottom of the hole 810, which can provide a large area for bone infiltration.

Figure 8C:
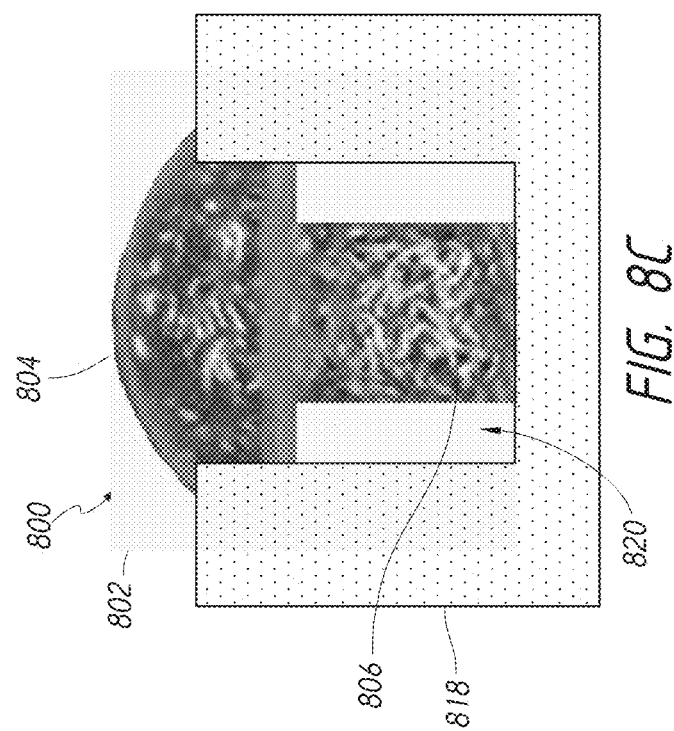
FIG. 8C schematically illustrates an example method of positioning an example implant.

FIG. 8C schematically illustrates an example method of positioning an example implant 800. In contrast to FIG. 8B, the hole 820 in the bone segment 818 is generally cylindrical throughout. The bottom of the first portion 802 can appose sidewalls of the hole 818. The hole 820 may be easier and/or faster to form than the hole 810 such that the hole 820 may be desired even if sidewall apposition by the third portion 806 is reduced or eliminated and Interaction between the sidewalls of the hole 810 and the edges of the implant 810 do not create a downward force. In some embodiments, a hole comprises a lower cylindrical portion having a first lateral dimension (e.g., diameter) sized to correspond to a lateral dimension (e.g., diameter) of the third portion 806 and an upper cylindrical portion having a second lateral dimension (e.g., diameter) larger than the first lateral dimension, which may be easier to form than the hole 810 and still provide sidewall apposition by the third portion 806.

FIG. 9A is a side view of an example implant 900. FIG. 9B is a cross-sectional view of the implant 900 of FIG. 9A. FIGS. 9C and 9D are top and side perspective exploded views of the implant 900 of FIG. 9A. Like several of the implants described herein, the implant 900 comprises, in a first part 901, hydrogel 902 and porous material 904. The hydrogel 902 may infiltrate pores of the porous material 904. As best seen in FIGS. 9B and 9D, the porous material 904 is generally annular. In some embodiments, the porous material 904 could be a solid disc (e.g., like the porous material of the implant 100).

The implant 900 also comprises a second part 908. The second part 908 comprises an annular rim, a bottom, and a barb 910. The rim and the bottom at least partially define a cavity configured to receive the first part 901. In some embodiments, the barb 910 is monolithic (formed from a single piece of material) with the remainder of the second part 908. In some embodiments, the barb 910 is formed separately from the remainder of the second part 908 and coupled to the remainder of the second part 908. The second part 908 may comprise a rigid material such as metal, ceramic, plastic, etc. The second part 908 may be formed, for example, by metal casting, injection molding, milling, printing, combinations thereof, etc.

The barb 908 may be inwardly compressible when longitudinally advanced, for example into a hole in a bone site, but configured to catch when longitudinally retracted, for example from a hole in a bone site. The second part 908 may comprise a porous material (e.g., to allow bone infiltration) and/or non-porous material (e.g., the second part 908 being anchored by the barb 908).

The second part 908 may be inserted at an implant site (e.g., a hole in a bone site) and the first part 901 may be inserted into the second part 908, and thus also into the implant site. As best seen in FIGS. 9B-9D, the porous material 904 comprises an annular groove 905 and the second part 908 comprises a detent 912. When the first part 901 is inserted into the second part 908, the porous material 904 and/or the detent 912 can flex until the detent 912 interacts with the groove 905, at which point the first part 901 is inhibited from being dislodged from the second portion 908. The groove 905 may be partially or fully annular. In some embodiments, the second part 908 comprises a plurality of detents 912 (e.g., two detents, three detents, four detents, five detents, six detents, ranges therebetween, or more than six detents). The circumferential spacing between detents 912 may be the same (e.g., spaced by about 360° divided by the number of detents) or may vary between pairs of detents 912.

Figure 9E:
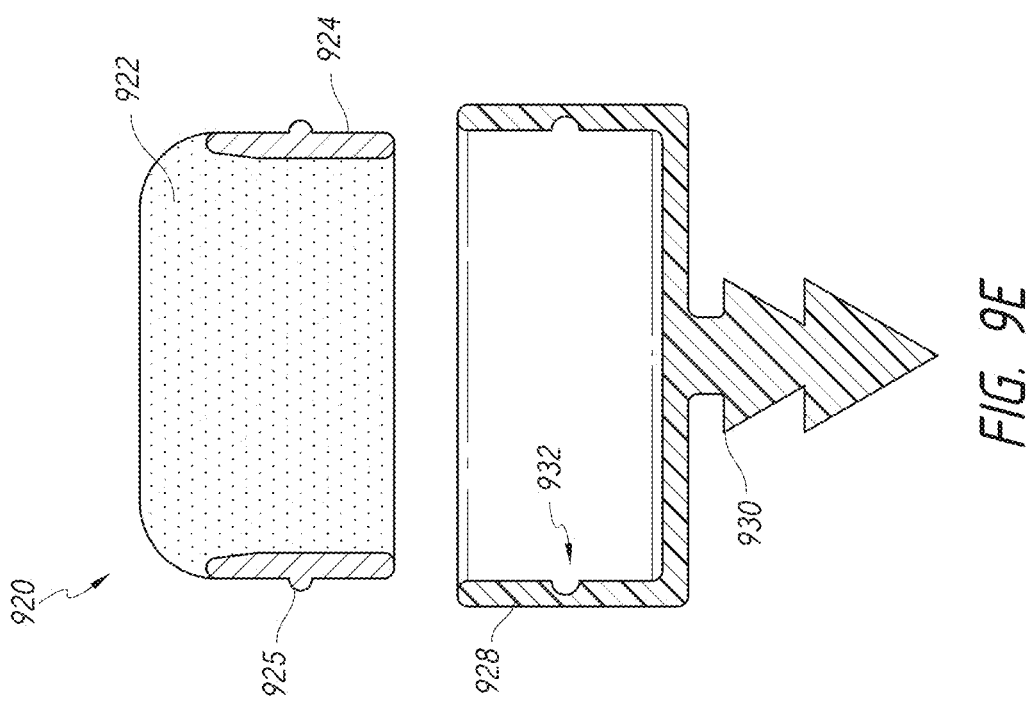
FIG. 9E is a cross-sectional view of an example implant.
Figure 9D:
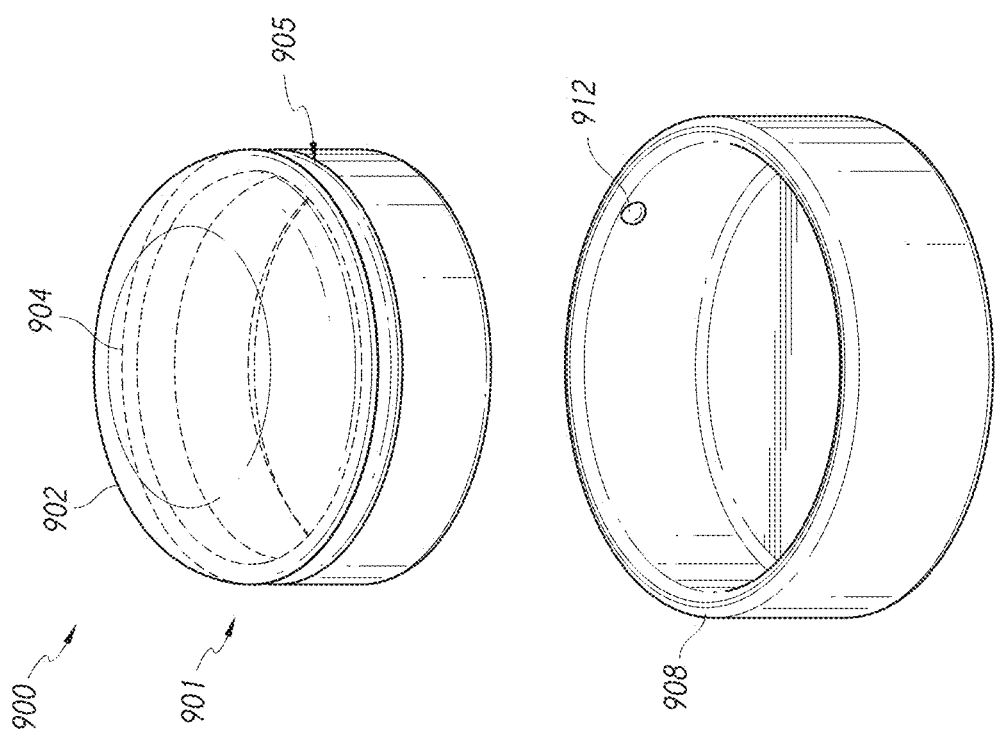

FIG. 9E is a cross-sectional view of an example implant 920. The implant 920 shares some features with the implant 900, for example comprising hydrogel 922, porous material 924, and a second part 928. The second part 928 comprises a barb 930 comprising two radially outward protrusions, which may provide better dislodge resistance than a single barb. Converse to the implant 900, in which the porous material 904 comprises a groove 905 and the second part 908 comprises a detent 912, in the implant 920, the porous material 924 comprises a detent 925 and the second part 928 comprises a groove 932. The groove 925 may be partially or fully annular. In some embodiments, the porous material 924 comprises a plurality of detents 925 (e.g., two detents, three detents, four detents, five detents, six detents, ranges therebetween, or more than six detents). The circumferential spacing between detents 925 may be the same (e.g., spaced by about 360° divided by the number of detents) or may vary between pairs of detents 925.

FIG. 10A is a side view of an example implant 1000. FIG. 10B is a cross-sectional view of the implant 1000 of FIG. 10A. FIGS. 10C-10E are top and side perspective exploded views of the implant 1000 of FIG. 10A. Like the implant 900, the implant 1000 comprises, in a first part 1001, hydrogel 1002 and porous material 1004. The hydrogel 1002 may infiltrate pores of the porous material 1004. As best seen in FIGS. 10B and 10E, the porous material 1004 is generally annular. In some embodiments, the porous material 1004 could be a solid disc (e.g., like the porous material of the implant 100).

The implant 1000 also comprises a second part 1008. The second part 1008 comprises an annular rim, a bottom, and an anchor 1010. The rim and the bottom at least partially define a cavity configured to receive the first part 1001. The second part 1008 may comprise a rigid material such as metal, ceramic, plastic, etc. The second part 1008 may be formed, for example, by metal casting, injection molding, milling, printing, combinations thereof, etc. The second part 1008 may comprise a porous material (e.g., to allow bone infiltration) and/or non-porous material (e.g., the second part 1008 being anchored by the barb 1008).

The anchor 1010 comprises an insert 1022 and radially outwardly extending fingers 1024. The anchor 1010 may be coupled to the second part 1008 by a wire 1026 extending through holes 1009 and forming a knot 1028. The anchor 1010 may be pushed into a hole (e.g., a hole in a bone site). The fingers 1024 may flex radially inwardly during advancement into the hole and flex radially outward to inhibit dislodgement from the hole. Ends of the wire 1026 may optionally form a loop. When ends of the wire 1026 are pulled, the knot 1028 tightens to draw the second part 1008 and the anchor 1010 closer together. The anchor 1010 is inhibited from retracting, so the tightening pushes the second part 1008 into the hole. In some embodiments, the anchor 1010 shares features with the anchors described in U.S. Patent Pub. No. 2015/0351815, which is incorporated herein by reference in its entirety for all purposes.

The second part 1008 may be inserted at an implant site (e.g., a hole in a bone site) and tightened, and the first part 1001 may be inserted into the second part 1008, and thus also into the implant site. As best seen in FIGS. 10B-10E, the porous material 1004 comprises an annular groove 1005 and the second part 1008 comprises a detent 1012. When the first part 1001 is inserted into the second part 1008, the porous material 1004 and/or the detent 1012 can flex until the detent 1012 interacts with the groove 1005, at which point the first part 1001 is inhibited from being dislodged from the second portion 1008. The groove 1005 may be partially or fully annular. In some embodiments, the second part 1008 comprises a plurality of detents 1012 (e.g., two detents, three detents, four detents, five detents, six detents, ranges therebetween, or more than six detents). The circumferential spacing between detents 1012 may be the same (e.g., spaced by about 360° divided by the number of detents) or may vary between pairs of detents 1012.

FIG. 10F is a cross-sectional view of an example implant 1040. The implant 1040 shares some features with the implant 1000, for example comprising hydrogel 1042, porous material 1044, and a second part 1048. The second part 1048 comprises an anchor 1050 including a loop 1060 proximal to a knot 1058. Converse to the implant 1000, in which the porous material 1004 comprises a groove 1005 and the second part 1008 comprises a detent 1012, in the implant 1040, the porous material 1044 comprises a detent 1045 and the second part 1048 comprises a groove 1052. The groove 1052 may be partially or fully annular. In some embodiments, the porous material 1044 comprises a plurality of detents 1045 (e.g., two detents, three detents, four detents, five detents, six detents, ranges therebetween, or more than six detents). The circumferential spacing between detents 1045 may be the same (e.g., spaced by about 360° divided by the number of detents) or may vary between pairs of detents 1045.

Figure 11C:
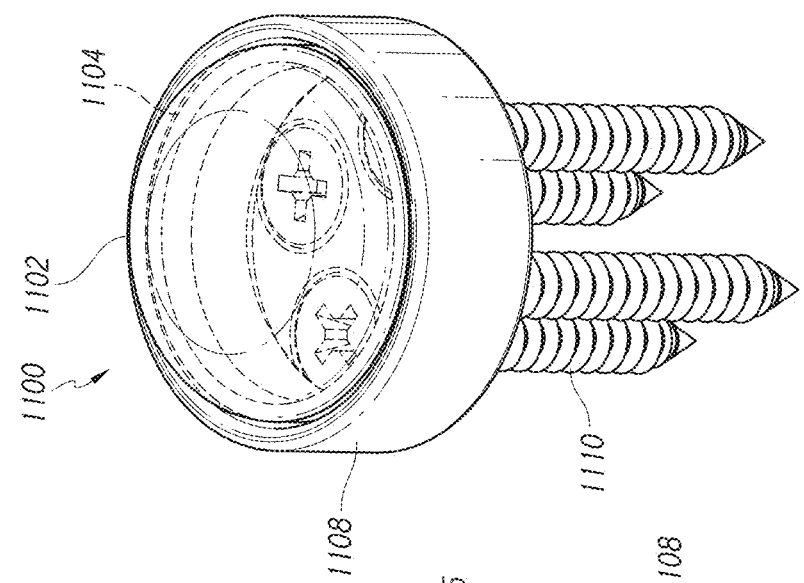
FIG. 11C is a top and side perspective view of the implant of FIG. 11A.
Figure 11B:
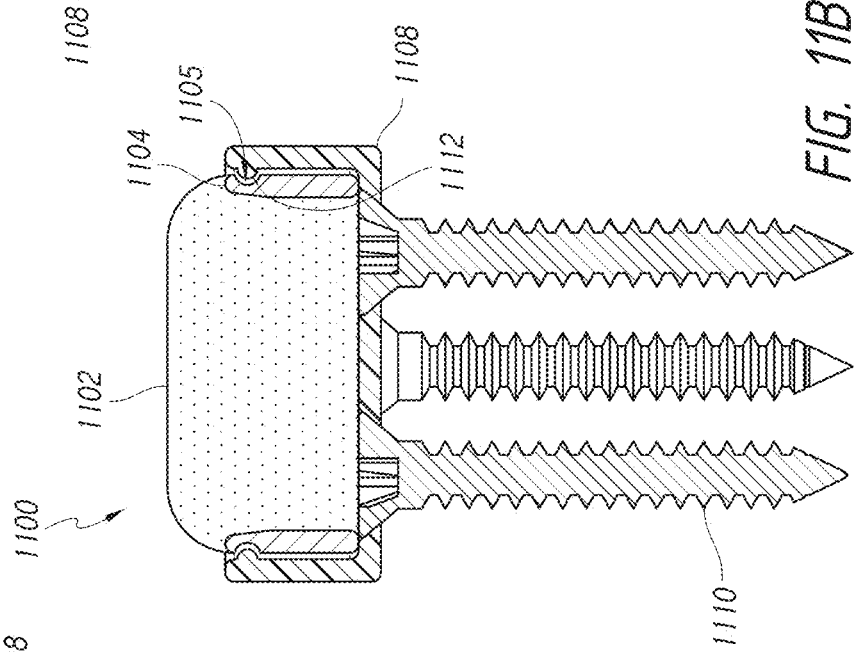
FIG. 11B is a cross-sectional view of the implant of FIG. 11A.
Figure 11A:
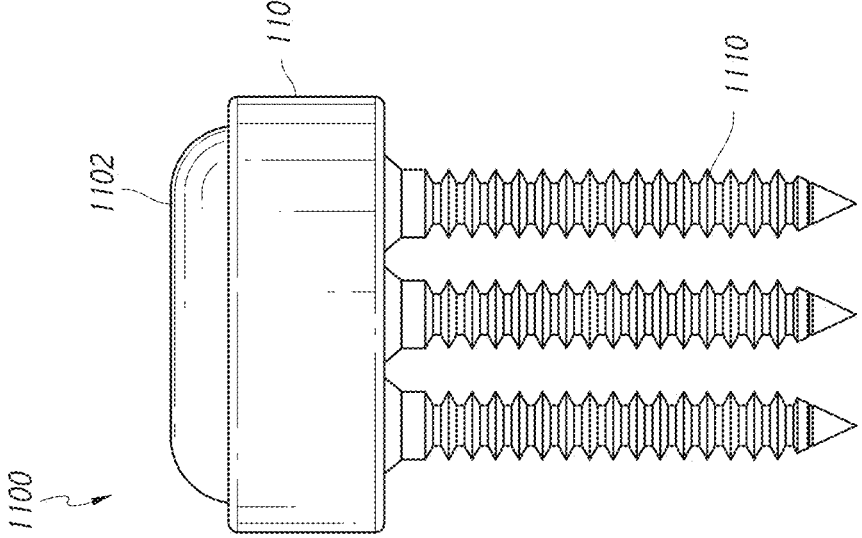
FIG. 11A is a side view of an example implant.

FIG. 11A is a side view of an example implant 1100. FIG. 11B is a cross-sectional view of the implant 1100 of FIG. 11A. FIG. 11C is a top and side perspective view of the implant 1100 of FIG. 11A. FIG. 11D is a top and side perspective exploded view of the implant 1100 of FIG. 11A. Like the implant 900, the implant 1100 comprises, in a first part 1101, hydrogel 1102 and porous material 1104. The hydrogel 1102 may infiltrate pores of the porous material 1104. As best seen in FIGS. 11B and 11D, the porous material 1104 is generally annular. In some embodiments, the porous material 1104 could be a solid disc (e.g., like the porous material of the implant 100).

The implant 1100 also comprises a second part 1108. The second part 1108 comprises an annular rim and a bottom. The rim and the bottom at least partially define a cavity configured to receive the first part 1101. The second part 1108 may comprise a rigid material such as metal, ceramic, plastic, etc. The second part 1108 may be formed, for example, by metal casting, injection molding, milling, printing, combinations thereof, etc. The second part 1108 may comprise a porous material (e.g., to allow bone infiltration) and/or non-porous material (e.g., the second part 1108 being anchored by the barb 1108).

The bottom of the second part 1108 comprises a plurality of holes 1109 configured to receive screws 1110. In some embodiments, the bottom of the second part 1108 comprises one hole 1109, two holes 1109, three holes 1109, four holes 1109 (e.g., as shown in FIG. 11D), five holes 1109, six holes 1109, ranges therebetween, or more than six holes.

The second part 1108 may be inserted at an implant site (e.g., a hole in a bone site). One or more screws 1010 may be inserted through holes 1109 to tighten the second part 1108 against the hole. The first part 1101 may be inserted into the second part 1108, and thus also into the implant site. As best seen in FIGS. 11B and 11D, the porous material 1104 comprises an annular groove 1105 and the second part 1108 comprises a detent 1112. When the first part 1101 is inserted into the second part 1108, the porous material 1104 and/or the detent 1112 can flex until the detent 1112 interacts with the groove 1105, at which point the first part 1101 is inhibited from being dislodged from the second portion 1108. The groove 1105 may be partially or fully annular. In some embodiments, the second part 1108 comprises a plurality of detents 1112 (e.g., two detents, three detents, four detents, five detents, six detents, ranges therebetween, or more than six detents). The circumferential spacing between detents 1112 may be the same (e.g., spaced by about 360° divided by the number of detents) or may vary between pairs of detents 1112.

Figure 11E:
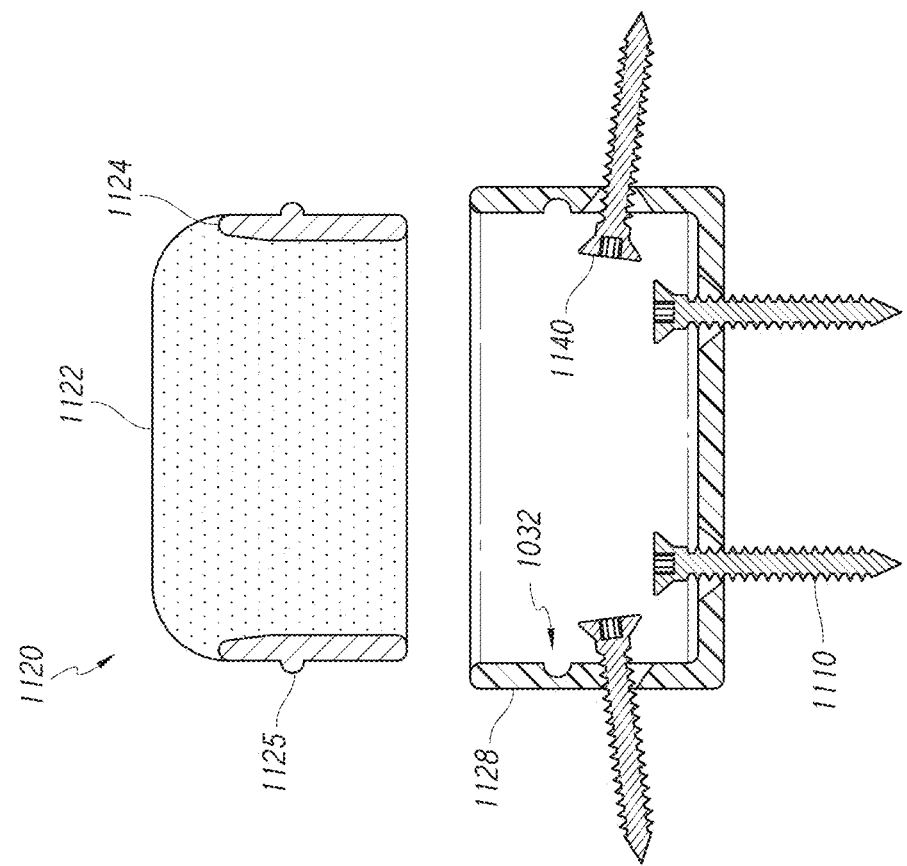
FIG. 11E is a cross-sectional view of an example implant.
Figure 11D:
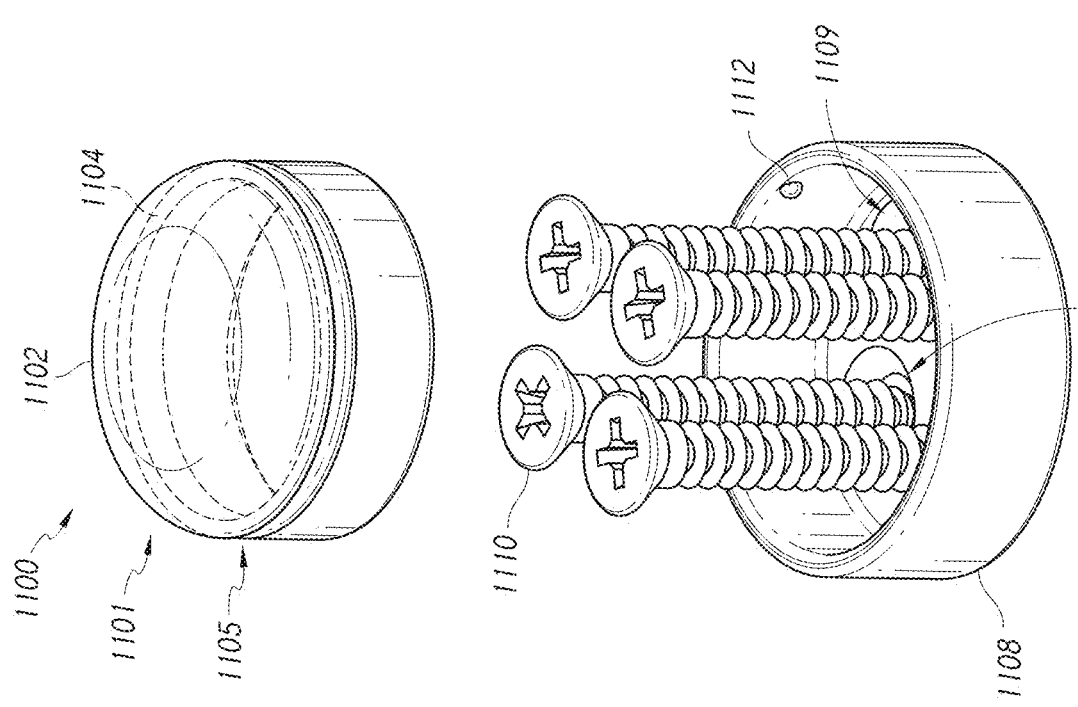
FIG. 11D is a top and side perspective exploded view of the implant of FIG. 11A.

FIG. 11E is a cross-sectional view of an example implant 1120. The implant 1120 shares some features with the implant 1100, for example comprising hydrogel 1122, porous material 1124, and a second part 1128. Like the implant 1100, the second part 1128 comprises a bottom including holes configured to receive screws 1110 therethrough. The second part 1128 also comprises holes in the sidewalls configured to receive screws 1140 therethrough. Inserting the screws 1140 in the sidewalls of the second part can provide more options for fixation of the second part 1128 at an implant site and/or better fixation than a second part comprising only bottom holes. Converse to the implant 1100, in which the porous material 1104 comprises a groove 1105 and the second part 1108 comprises a detent 1112, in the implant 1120, the porous material 1124 comprises a detent 1125 and the second part 1128 comprises a groove 1132. The groove 1132 may be partially or fully annular. In some embodiments, the porous material 1124 comprises a plurality of detents 1125 (e.g., two detents, three detents, four detents, five detents, six detents, ranges therebetween, or more than six detents). The circumferential spacing between detents 1125 may be the same (e.g., spaced by about 360° divided by the number of detents) or may vary between pairs of detents 1115.

FIG. 12A is a side cross-sectional view of an example implant 1200. Like the implant 900, the implant 1200 comprises hydrogel 1202 and porous material 1204. The hydrogel 1202 may infiltrate pores of the porous material 1204. The porous material 1204 is generally annular. In some embodiments, the porous material 1204 could be a solid disc (e.g., like the porous material of the implant 100). The porous material 1204 comprises a detent 1206 configured to interact with or "bite" the hydrogel 1202. The detent 1206 may be partially or fully annular. In some embodiments, the porous material 1204 comprises a plurality of detents 1206, for example at a variety of positions along the inner walls of the porous material 1204. In some embodiments, the porous material 1204 may comprise a non-porous material, for example because the bite of the detent 1206 provides sufficient interaction with the hydrogel 1202 to inhibit dislodgement of the hydrogel 1202. The porous material 1204 further comprises a barb 1208. The barb 1208 may be inwardly compressible (e.g., due to being thin and/or porous) when longitudinally advanced, for example into a hole in a bone site, but configured to catch when longitudinally retracted, for example from a hole in a bone site. The barb 1208 may be partially or completely annular. The porous material 1204 may comprise barbs 1208 at different longitudinal positions. In some embodiments, the porous material 1204 may be 3D printed, machined, etc.

The height of the porous material 1204 may be at least partially based on the intended use of the implant 1200. For example, if the intended use is a small joint (e.g., in a hand or foot), a larger profile and a less proud hydrogel 1202 generally reduces the chances of dislocation.

FIG. 12B is a side cross-sectional view of an example implant 1210. Like the implant 1200, the implant 1210 comprises hydrogel 1212 and porous material 1214 comprising a barb 1218. The porous material 1214 comprises a groove into which the hydrogel 1212 can radially outwardly extend to form a detent 1216 or a flange if fully annular. The interaction between the detent 1216 and the porous material 1214 provides sufficient bite that the porous material 1214 may comprise a non-porous material. Depending on the mold, desirability of the detent 1216 extending radially outward of the porous material 1214, etc., the detent 1216 may be trimmed.

FIG. 12C is a side cross-sectional view of an example implant 1220. Like the implant 1200, the implant 1220 comprises hydrogel 1222 and porous material 1224 comprising a detent 1226. The porous material 1224 lacks or is free of a barb, but the porous material 1224 may interact with sidewalls of a hole at an implant site to allow bone infiltration. The implant 1220 may comprise a hydrogel detent like the implant 1210. Any of the implants 1200, 1210, 1220 may comprise porous material detents, hydrogel detents, or combinations thereof.

Figure 12D:
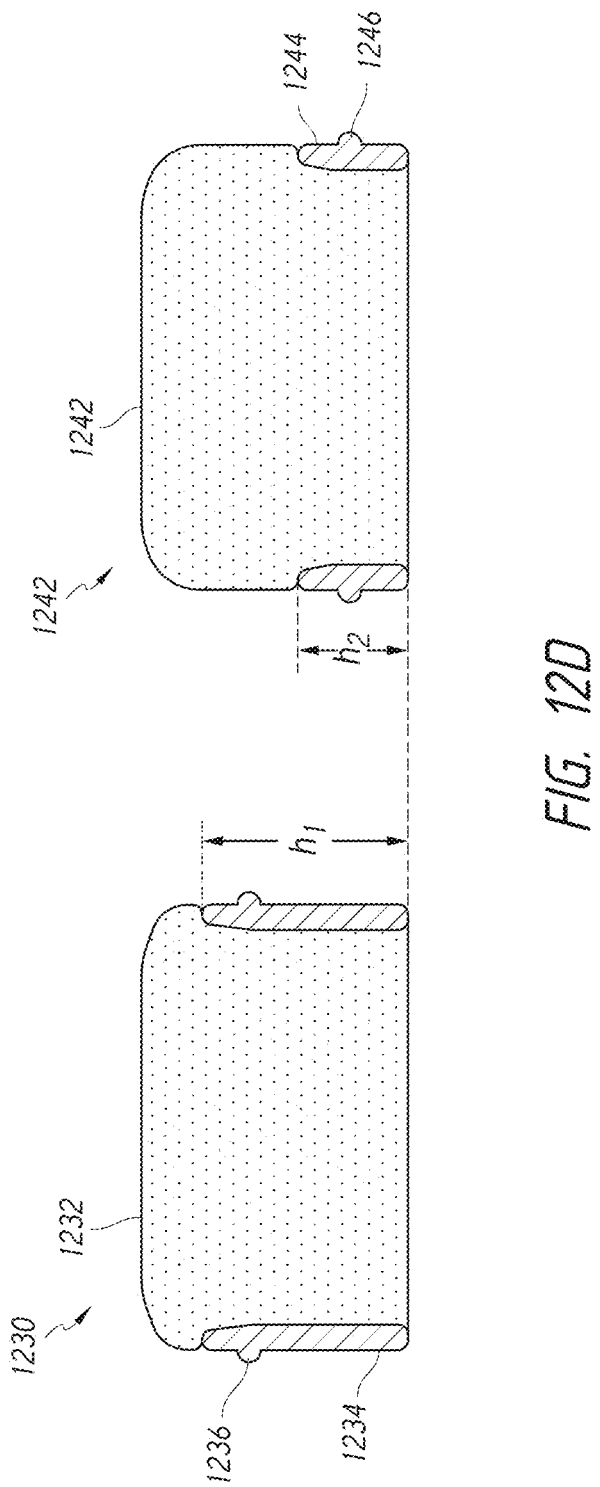
FIG. 12D is a side cross-sectional view of example implants.

FIG. 12D is a side cross-sectional view of example implants 1230, 1240. The implant 1230 comprises hydrogel 1232 and porous material 1234. The hydrogel 1232 infiltrates the pores of the porous material 1234. The porous material 1234 comprises a detent 1236 configured to engage a groove, for example in a second part and/or in a bone hole at an implant site. The porous material 1234 has a height $h_1$. The hydrogel 1232 is proud over the porous material 1234. The implant 1240 comprises hydrogel 1242 and porous material 1244. The hydrogel 1242 infiltrates the pores of the porous material 1244. The porous material 1244 comprises a detent 1246 configured to engage a groove, for example in a second part and/or in a bone hole at an implant site. The porous material 1244 has a height $h_2$ less than the height $h_1$. The hydrogel 1242 is proud over the porous material 1244. The implant 1240 may provide more hydrogel 1242 to appose sidewalls of a second part and/or a bone hole at an implant site. If the bone stock and/or density is limited, the height of the porous material may be increased, which can provide column strength in the implant. If bone stock and/or density is favorable, the height of the porous material may be reduced, which can allow more hydrogel apposition of sidewalls.

With respect to any of the implants described herein in which the porous material comprises metal, the implant may advantageously be visible under x-ray.

With respect to any of the implants described herein, comprising porous material allowing fixation due to bone infiltration and/or comprising a fixation device such as a barb, anchor, screw, etc., an overall height can be reduced versus and implant, for example, consisting essentially of hydrogel (e.g., lacking porous material and/or a fixation device), which generally uses interaction between a long bone hole and a large height to provide anti-dislodging force. In some embodiments, an anchored implant can have a height that is less than a height of an equivalent but unanchored implant by about 10% to about 60% (e.g., about 10%, about 20%, about 30%, about 40%, about 50%, about 60%, ranges between such values, etc.). For example, if a hydrogel implant has a diameter of 10 mm and a height of 10 mm, then an implant as described herein may have a diameter of 10 mm and a height of 5 mm such that the height is 50% less.

Figure 13B:
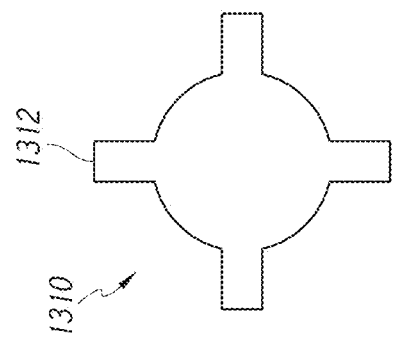
FIG. 13B is plan view of an example device for manufacturing example implants.
Figure 13A:
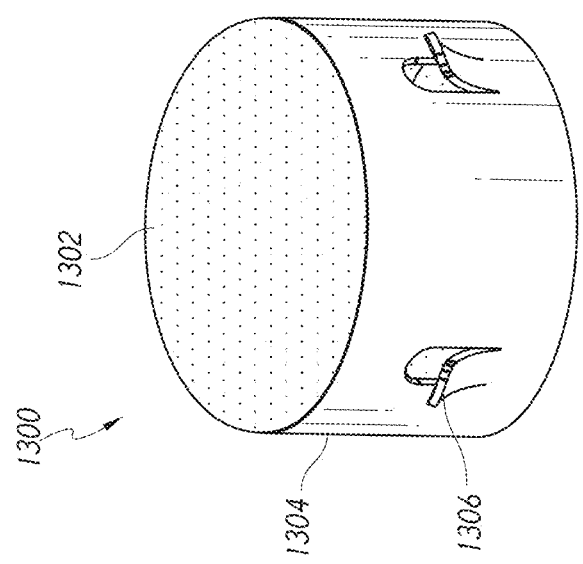
FIG. 13A is a top and side perspective view of an example implant.

FIG. 13A is a top and side perspective view of an example implant 1300. The implant 1300 comprises hydrogel 1302 and porous material 1304. The hydrogel 1302 infiltrates pores of the porous material 1304. The porous material 1304 comprises radially outward and upward extending fingers 1306. Similar to the anchor 1010 of the implant 1000 described herein, the fingers 1306 may flex radially inwardly during advancement of the implant 1300 into a bone hole at an implant site and flex radially outward to inhibit dislodgement from the hole. In some embodiments, the fingers 1306 and general structure of the device 1300 share features with the anchors described in U.S. Patent Pub. No. 2015/0351815. The hydrogel 1302 may extend radially outward towards the fingers 1306.

FIG. 13B is plan view of an example device 1310 for manufacturing example implants such as the implant 1300. In some embodiments, the device 1310 comprises a hydrogel mold. The device 1310 comprises a plurality of radially outwardly extending arms 1312 configured to accommodate hydrogel that can infiltrate cutouts forming the fingers 1306. For example, with reference to FIGS. 4-5C and 13A, a porous material 1304 comprising a plurality of fingers 1306 can be placed into the device 1310. The device 1310 may be filled with hydrogel 1302, which can infiltrate pores of the porous material 1304 to form the implant 1300.

Although several embodiments and examples are disclosed herein, the present application extends beyond the specifically disclosed embodiments to other alternative embodiments and/or uses of the various inventions and modifications, and/or equivalents thereof. It is also contemplated that various combinations or subcombinations of the specific features and aspects of the embodiments may be made and still fall within the scope of the inventions. Accordingly, various features and aspects of the disclosed embodiments can be combined with or substituted for one another in order to form varying modes of the disclosed inventions. Thus, the scope of the various inventions disclosed herein should not be limited by any particular embodiments described above. While the embodiments disclosed herein are susceptible to various modifications, and alternative forms, specific examples thereof have been shown in the drawings and are described in detail herein. However, the inventions of the present application are not limited to the particular forms or methods disclosed, but, to the contrary, cover all modifications, equivalents, and alternatives falling within the spirit and scope of the various embodiments described and the appended claims. Further, the disclosure herein of any particular feature, aspect, method, property, characteristic, quality, attribute, element and/or the like in connection with an implementation or embodiment can be used in all other implementations or embodiments set forth herein.

In any methods disclosed herein, the acts or operations can be performed in any suitable sequence and are not necessarily limited to any particular disclosed sequence and not be performed in the order recited. Various operations can be described as multiple discrete operations in turn, in a manner that can be helpful in understanding certain embodiments; however, the order of description should not be construed to imply that these operations are order dependent. Additionally, any structures described herein can be embodied as integrated components or as separate components. For purposes of comparing various embodiments, certain aspects and advantages of these embodiments are described. Not necessarily all such aspects or advantages are achieved by any particular embodiment. Thus, for example, embodiments can be carried out in a manner that achieves or optimizes one advantage or group of advantages without necessarily achieving other advantages or groups of advantages.

The methods disclosed herein include certain actions taken by a practitioner; however, they can also include any third-party instruction of those actions, either expressly or by implication. For example, actions such as "deploying an implant" include "instructing deployment of an implant." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 mm" includes "1 mm." Phrases preceded by a term such as "substantially" include the recited phrase and should be interpreted based on the circumstances (e.g., as much as reasonably possible under the circumstances). For example, "substantially rigid" includes "rigid" and "substantially parallel" includes "parallel."

What is claimed is:

1. An implant configured for implantation in a hole prepared in a bone segment, the implant comprising:
   a first portion comprising a hydrogel;
   a second portion comprising a porous material and the hydrogel in pores of the porous material:
   a third portion comprising the porous material; and
   an anchor extending through the porous material in the second and the third portions and protruding from the third portion in a direction away from the first portion, wherein the hole has a bottom surface and when the implant is inserted into the hole, the anchor maintains a downward force on the third portion against the bottom of the hole.

2. The implant of claim 1, wherein the anchor comprises barbs that flare outward.

3. The implant of claim 1, wherein the hole in the bone segment comprises a secondary hole in the bottom surface and when the implant is inserted into the hole, the anchor fits into the secondary hole.

4. The implant of claim 3, wherein the anchor comprises barbs that flare outward and can flex inwardly during insertion into the secondary hole thus resisting retraction of the anchor.

5. The implant of claim 1, wherein the porous material in the second portion and the third portion comprises a grommet shape including an eyelet and the anchor extends through the eyelet.

6. The implant of claim 1, wherein the implant comprises a plurality of anchors.

7. The implant of claim 6, wherein the porous material in the second portion and the third portion comprises a plurality of eyelets for the plurality of anchors.

8. The implant of claim 1, wherein the third portion has non-uniform lateral cross-section.

9. The implant of claim 8, wherein the bottom of the third portion has a non-uniform lateral cross-section.

10. The implant of claim 8, wherein the bottom of the third portion has an ellipse shape having a length greater than a width.

\* \* \* \* \*